(12) United States Patent
Lieberman

(10) Patent No.: US 7,740,635 B2
(45) Date of Patent: Jun. 22, 2010

(54) MINIMALLY INVASIVE METHOD AND APPARATUS FOR PLACING FACET SCREWS AND FUSING ADJACENT VERTEBRAE

(75) Inventor: Isador H. Lieberman, Pepper Pike, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 1027 days.

(21) Appl. No.: 11/156,903

(22) Filed: Jun. 20, 2005

(65) Prior Publication Data

US 2006/0079908 A1 Apr. 13, 2006

Related U.S. Application Data

(63) Continuation-in-part of application No. 10/952,650, filed on Sep. 29, 2004.

(51) Int. Cl.
*A61B 17/58* (2006.01)
*A61B 17/60* (2006.01)
*A61F 2/00* (2006.01)

(52) U.S. Cl. .............. 606/104; 606/247; 606/86 R; 606/96

(58) Field of Classification Search ............ 606/99, 606/279, 914–916, 86 R, 59
See application file for complete search history.

(56) References Cited

U.S. PATENT DOCUMENTS

| | | | | |
|---|---|---|---|---|
| 1,201,864 | A * | 10/1916 | Overmeyer | 606/54 |
| 4,662,365 | A * | 5/1987 | Gotzen et al. | 606/59 |
| 5,219,349 | A * | 6/1993 | Krag et al. | 606/53 |
| 5,676,664 | A * | 10/1997 | Allard et al. | 606/57 |
| 5,746,741 | A * | 5/1998 | Kraus et al. | 606/54 |
| 6,287,313 | B1 | 9/2001 | Sasso | |
| 6,485,518 | B1 | 11/2002 | Cornwall et al. | |
| 6,530,930 | B1 | 3/2003 | Marino et al. | |
| 6,547,795 | B2 | 4/2003 | Schneiderman | |
| 6,562,046 | B2 | 5/2003 | Sasso | |
| 6,652,523 | B1 * | 11/2003 | Evrard et al. | 606/54 |
| 6,669,698 | B1 | 12/2003 | Tromanhauser et al. | |
| 2002/0007188 | A1 | 1/2002 | Arambula et al. | |

OTHER PUBLICATIONS

U.S. Lieberman U.S. Appl. No. 10/952,654, filed Sep. 29, 2004 entitled Minimally Invasive Method and Apparatus for Fusing Adjacent Vertebrae.

(Continued)

*Primary Examiner*—Thomas C Barrett
*Assistant Examiner*—Andrew Yang
(74) *Attorney, Agent, or Firm*—Tarolli, Sundheim, Covell & Tummino LLP

(57) ABSTRACT

A minimally invasive apparatus for placing screws across a facet joint between first and second vertebrae comprises a first K-wire for inserting into a spinous process of the first vertebrae and a first fixation block removably connected to the first K-wire. The apparatus has a second K-wire for inserting into a transverse process of the second vertebrae and a second fixation block removably connected to the second K-wire. A first rod member is removably connected to both of the first and second fixation blocks. A support apparatus further secures the first and second K-wires to the first and second vertebrae. The apparatus has a cannula that enables implantation of the translaminar screws across a facet joint between the first and second vertebrae.

17 Claims, 25 Drawing Sheets

OTHER PUBLICATIONS

Grob et al. (1998) Translaminar Screw Fixation in the Lumbar Spine: Technique, Indications, Results, Eur. Spine J. 7:178-186.
Jang et al., (2003) Guide Device for Percutaneous Placement of Translaminar Facet Screws After Anterior Lumbar Interbody Fusion, J. Neurosurg (Spine 1) 98:100-103.

* cited by examiner

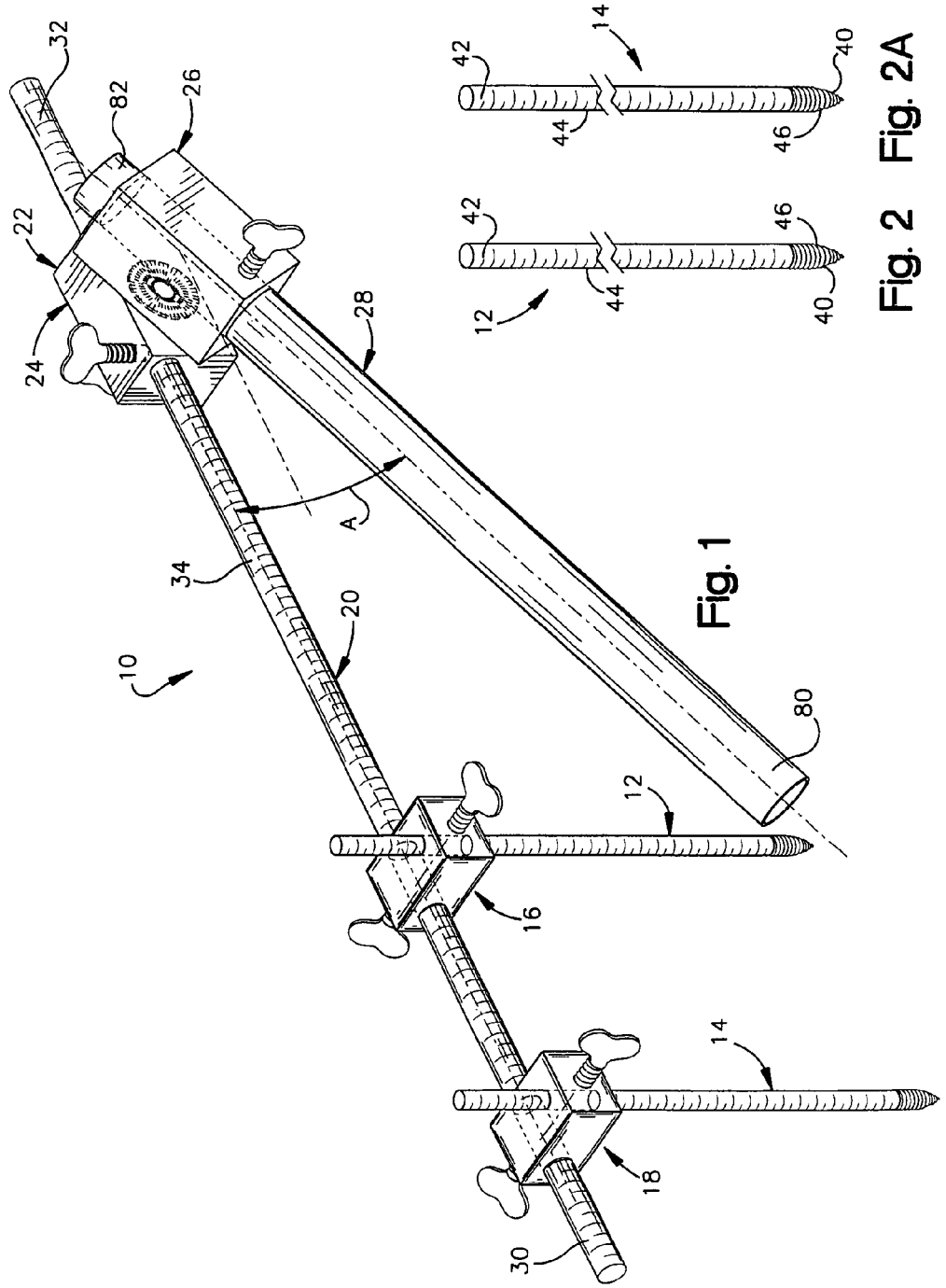

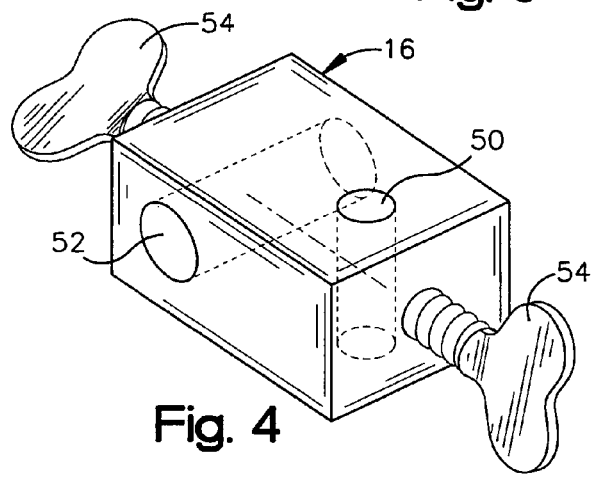
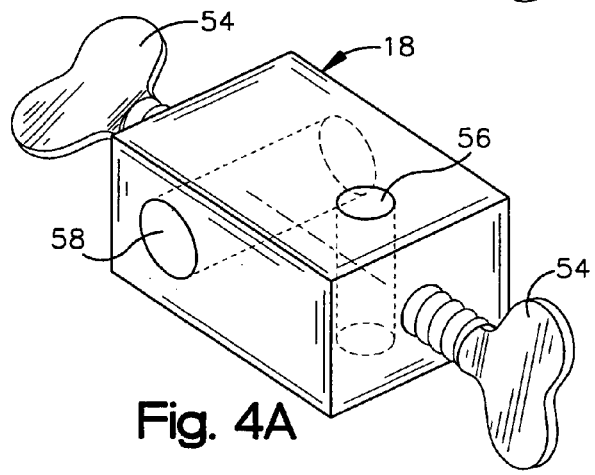
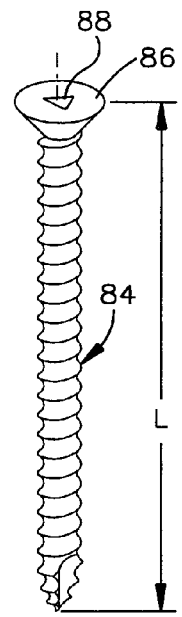
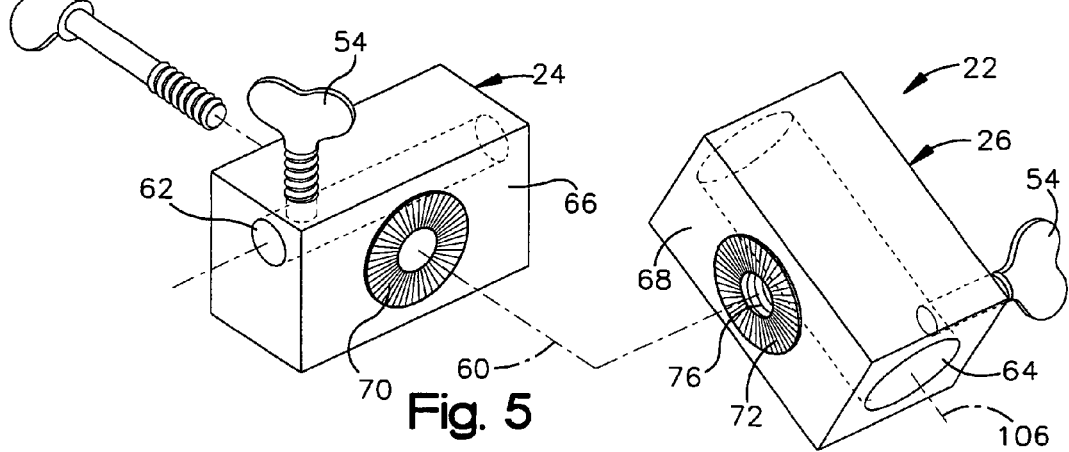

MINIMALLY INVASIVE METHOD AND APPARATUS FOR PLACING FACET SCREWS AND FUSING ADJACENT VERTEBRAE

RELATED APPLICATION

This application is a continuation-in-part of a co-pending U.S. patent application Ser. No. 10/952,650, entitled "MINIMALLY INVASIVE METHOD AND APPARATUS FOR PLACING FACET SCREWS AND FUSING ADJACENT VERTEBRAE", filed Sep. 29, 2004. The subject matter of the aforementioned co-pending application is incorporated herein by reference.

TECHNICAL FIELD

The present invention relates to a minimally invasive method and apparatus for placing facet screws and fusing adjacent vertebrae.

BACKGROUND OF THE INVENTION

Over 200,000 spinal fixation and spinal fusion procedures are performed annually to correct various congenital and degenerative spinal disorders in humans. Many of these corrective surgical procedures are performed in the lumbar and lumbosacral regions of the spine where traumatic and age-related disc degeneration is common. One such procedure involves the implantation of spinal fixation instrumentation, including plates and rods, using pedicle screws. Another procedure involves the implantation of one or more anterior fusion cages into the intervertebral disc space following a discectomy. These and other known spinal fixation and/or fusion procedures can be quite invasive, traumatic, and time consuming. Further, problems with post-operative stability and pseudoarthrosis are often associated with many of these procedures.

It is well known that the two facet joints, which are formed between each pair of adjacent vertebrae, share and support the axial load on the spine with a respective intervertebral disc. Accordingly, it has been suggested to place screws either directly across the facet joints of adjacent vertebrae or indirectly across the facet joints through the lamina (i.e. translaminar) as both a primary means for spinal fixation and as a secondary means for fixation to augment anterior fusion. Indeed, this suggestion has been accepted by many surgeons as facet screws (direct and translaminar) are now being implanted on a regular basis. In order to further improve upon the use of such facet screws, a minimally invasive method and apparatus for accurately and repeatably placing the facet screws for implantation across the facet joints is needed.

SUMMARY OF THE INVENTION

The present invention is a minimally invasive apparatus for placing screws across a facet joint between adjacent first and second vertebrae. The apparatus comprises a first K-wire for inserting into the spinous process of the first vertebrae and a first fixation block removably connected to the first K-wire. The apparatus further comprises a second K-wire for inserting into a transverse process of the second vertebrae and a second fixation block removably connected to the second K-wire. A rod member is removably connected to both of the first and second fixation blocks. A swivel block assembly comprises relatively movable first and second block members. The rod member is removably connected to the first block member. A cannula extends from the second block member. The screws are insertable through the cannula for implantation across the facet joint.

In accordance with one aspect of the invention, each of the first and second K-wires includes means for measuring axial length along the K-wires.

In accordance with another aspect of the invention, the rod member includes means for measuring axial length along the rod member.

In accordance with another aspect of the invention, the swivel block assembly includes positioning means for controllably adjusting the angular position of the first and second block members relative to each other.

The present invention further includes an apparatus for placing translaminar screws across a facet joint between adjacent first and second vertebrae in a minimally invasive surgical procedure. The apparatus comprises a first K-wire for inserting into the spinous process of the first vertebrae and a second K-wire for inserting into a transverse process of the second vertebrae. The apparatus further includes first and second fixation blocks having perpendicularly extending first and second passages. The first K-wire extends into the first passage in the first fixation block and the second K-wire extending into the first passage in the second fixation block. A rod member extends through the second passage in the first fixation block and through the second passage in the second fixation block. A swivel block assembly comprises relatively movable first and second block members. The swivel block assembly includes a third passage extending through the first block member and a fourth passage extending through the second block member. The rod member extends into the third passage. A cannula extends into the fourth passage in the second block member. The translaminar screws are insertable through the cannula for implantation across a facet joint between the first and second vertebrae.

In accordance with one aspect of the invention, the first and second passages in the first fixation block are offset from each other by a predetermined amount. In accordance with another aspect of the invention, the first and second passages in the second fixation block are offset from each other by the predetermined amount.

The present invention further provides a minimally invasive surgical method for fusing adjacent upper and lower vertebrae. The method utilizes an apparatus comprising first and second K-wires, first and second fixation blocks, a swivel block having relatively movable first and second block members, a rod member extending between the fixation blocks and the first block member, and a cannula extending from the second block member. The first K-wire is inserted into the center of the spinous process of the upper vertebrae. The second K-wire is inserted into a transverse process on a first side of the lower vertebrae. The first fixation block is secured to the first K-wire and the second fixation block is secured to the second K-wire with the rod member extending across the K-wires. The second block member of the swivel block assembly is secured relative to the first block member to achieve a desired angle for a first axis along which a first screw will be implanted into the facet joint on the first side. The swivel block assembly is secured at a desired axial position on the rod member. Percutaneous access to the second side of the upper vertebrae along the first axis is then obtained via the cannula. A first screw is inserted through the cannula along the first axis and implanted across the facet joint on the first side to attach the upper and lower vertebrae.

In accordance with additional aspects of the inventive method, the cannula is moved to aim the cannula toward the facet joint on the second side of the vertebrae along a second axis. Percutaneous access along the second axis is then obtained to the facet joint on the second side via the cannula and a bone graft material is placed into the facet joint on the second side through the cannula to assist with fusion of the upper and lower vertebrae.

In accordance with a further aspect of the inventive method, a burring bit is inserted into the cannula and used to burr the articular surfaces of the facet joint on the second side to widen the facet joint for accepting the bone graft material.

In accordance with still other aspects of the inventive method, the cannula is removed from percutaneous insertion and the second K-wire is removed from the transverse process on the first side of the lower vertebrae. The second K-wire is then inserted into the transverse process on the second side of the lower vertebrae. The second fixation block is then secured to the second K-wire. Next, the first fixation block is released from the first K-wire and is rotated with the rod member extending across the K-wires. The first fixation block is secured to the first K-wire. The second block member of the swivel block assembly is then secured relative to the first block member to achieve a desired angle for a third axis along which a second screw will be implanted into the facet joint on the second side. The swivel block assembly is secured at a desired axial position along the rod member. Percutaneous access to the first side of the upper vertebrae is obtained via the cannula. A second screw is inserted through the cannula and implanted along the third axis across the facet joint on the second side to attach the upper and lower vertebrae.

In accordance with additional aspects of the inventive method, the cannula is moved to aim the cannula along a fourth axis toward the facet joint on the first side previously secured with the first screw. Percutaneous access to the facet joint on the first side is obtained via the cannula and a bone graft material is placed through the cannula into the facet joint around the previously implanted first screw to assist with fusion of the upper and lower vertebrae.

The present invention also provides a minimally invasive surgical method for placing screws through the lamina and across the facet joints between adjacent upper and lower vertebrae. The inventive method utilizes an apparatus comprising first and second K-wires, first and second fixation blocks, a swivel block having relatively movable first and second block members, a rod member extending between the fixation blocks and the first block member, and a cannula extending from the second block member. The first K-wire is inserted into the center of the spinous process of the upper vertebrae. The second K-wire is inserted into a transverse process on a first side of the lower vertebrae so that the second K-wire is parallel to the first K-wire in both the sagittal and coronal planes. The first fixation block is secured to the first K-wire and the second fixation block to the second K-wire with the rod member extending across the K-wires. A desired axial position is calculated for the swivel block assembly along the rod member. A desired angle for the centerline of the cannula is calculated to extend from a second side of the vertebrae toward the facet joint on the first side along a first axis. The second block member of the swivel block assembly is secured relative to the first block member to achieve the desired angle for the first axis. The swivel block assembly is secured at the desired axial position along the rod member. Percutaneous access to the junction of the lumina and the spinous process on the second side of the upper vertebrae is then obtained via the cannula. A first screw is inserted through the cannula. The first screw is implanted along the first axis across the facet joint on the first side to attach the upper and lower vertebrae.

In accordance with additional aspects of the inventive method, the cannula is removed from percutaneous insertion on the second side and the second K-wire is removed from the transverse process on first side of the lower vertebrae. The second K-wire is then re-inserted into the transverse process on the second side of the lower vertebrae so that the second K-wire is again parallel to the first K-wire in both the sagittal and coronal planes. The second fixation block is secured to the second K-wire. The first fixation block is released from the first K-wire and is rotated with the rod member extending across the K-wires. The first fixation block is then secured to the first K-wire. A desired axial position is calculated for the swivel block assembly along the rod member and the swivel block assembly is secured at the desired axial position. A desired angle is calculated for the centerline of the cannula to extend from the first side of the vertebrae toward the facet joint on the second side along a third axis. The second block member of the swivel block assembly is then secured relative to the first block member to achieve the desired angle. Percutaneous access to the junction of the lamina and the spinous process on the first side of the upper vertebrae is obtained via the cannula and a second screw is inserted into the cannula. The second screw is implanted along the third axis across the facet joint on the second side to attach the upper and lower vertebrae.

In accordance with further aspects of the inventive method, the cannula is moved from its position over the lamina on the first side of the upper vertebrae and the first and second block members are released to allow relative movement. The second block member is swiveled to aim the centerline of the cannula along a fourth axis toward the facet joint on the first side previously secured with the first screw. Percutaneous access to the facet joint on the first side is obtained via the cannula and a bone graft material is placed through the cannula into the facet joint on the first side around the previously implanted first screw to assist with fusion of the upper and lower vertebrae.

An example apparatus in accordance with the present invention places translaminar screws across a facet joint between adjacent first and second vertebrae in a minimally invasive surgical procedure. The apparatus includes a first K-wire, a second K-wire, a first fixation block, a second fixation block, a support block, a first rod member, a second rod member, and a cannula. The first K-wire is inserted into the spinous process of the first vertebrae. The second K-wire is inserted into a transverse process of the second vertebrae. The first fixation block has perpendicularly extending first and second passages. The first K-wire extends into the first passage in the first fixation block. The second fixation block has perpendicularly extending first and second passages. The second K-wire extends into the first passage in the second fixation block. The support block has perpendicularly extending first and second passages. The first K-wire extends into the first passage in the support block. The first rod member extends through the second passage in the first fixation block and the second passage in the second fixation block. The second rod member further secures the first and second fixation blocks to the first and second vertebrae. The second rod member extends through the second passage in the support block. The cannula enables implantation of the translaminar screws across a facet joint between the first and second vertebrae.

An example minimally invasive apparatus in accordance with the present invention places screws across a facet joint between adjacent first and second vertebrae in a minimally invasive surgical procedure. The apparatus includes a first K-wire, a second K-wire, a first fixation block, a second fixation block, a support block, a first rod member, a support apparatus, and a cannula. The first K-wire is inserted into a spinous process of the first vertebrae. The first fixation block is removably connected to the first K-wire. The second K-wire is inserted into a transverse process of the second vertebrae. The second fixation block is removably connected to the second K-wire. The first rod member is removably connected to both of the first and second fixation blocks. The support apparatus further secures the first and second K-wires to the first and second vertebrae. The cannula enables implanting of the screws across the facet joint between the first and second vertebrae.

Another example apparatus in accordance with the present invention places screws through a cannula and across a facet joint between adjacent first and second vertebrae. The apparatus includes a first K-wire, a first fixation block, a second K-wire, a second fixation block, a rod member, and a support apparatus. The first K-wire is inserted into a spinous process of the first vertebrae. The first fixation block is removably connected to the first K-wire. The second K-wire is inserted into a transverse process of the second vertebrae. The second fixation block is removably connected to the second K-wire. The first rod member is removably connected to both the first and second fixation blocks. The support apparatus further secures the first and second K-wires to the first and second vertebrae.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is a perspective view of an apparatus for placing facet screws in accordance with the present invention;

FIG. 2 is a perspective view of a component of the apparatus of FIG. 1;

FIG. 2A is a perspective view of a component of the apparatus of FIG. 1;

FIG. 3 is a perspective view of another component of the apparatus of FIG. 1;

FIG. 4 is a perspective view of another component of the apparatus of FIG. 1;

FIG. 4A is a perspective view of another component of the apparatus of FIG. 1;

FIG. 5 is an exploded perspective view of another component of the apparatus of FIG. 1;

FIG. 6 is a perspective view of a screw to be implanted in accordance with the present invention;

DESCRIPTION OF EXAMPLE EMBODIMENTS

Figure 7:
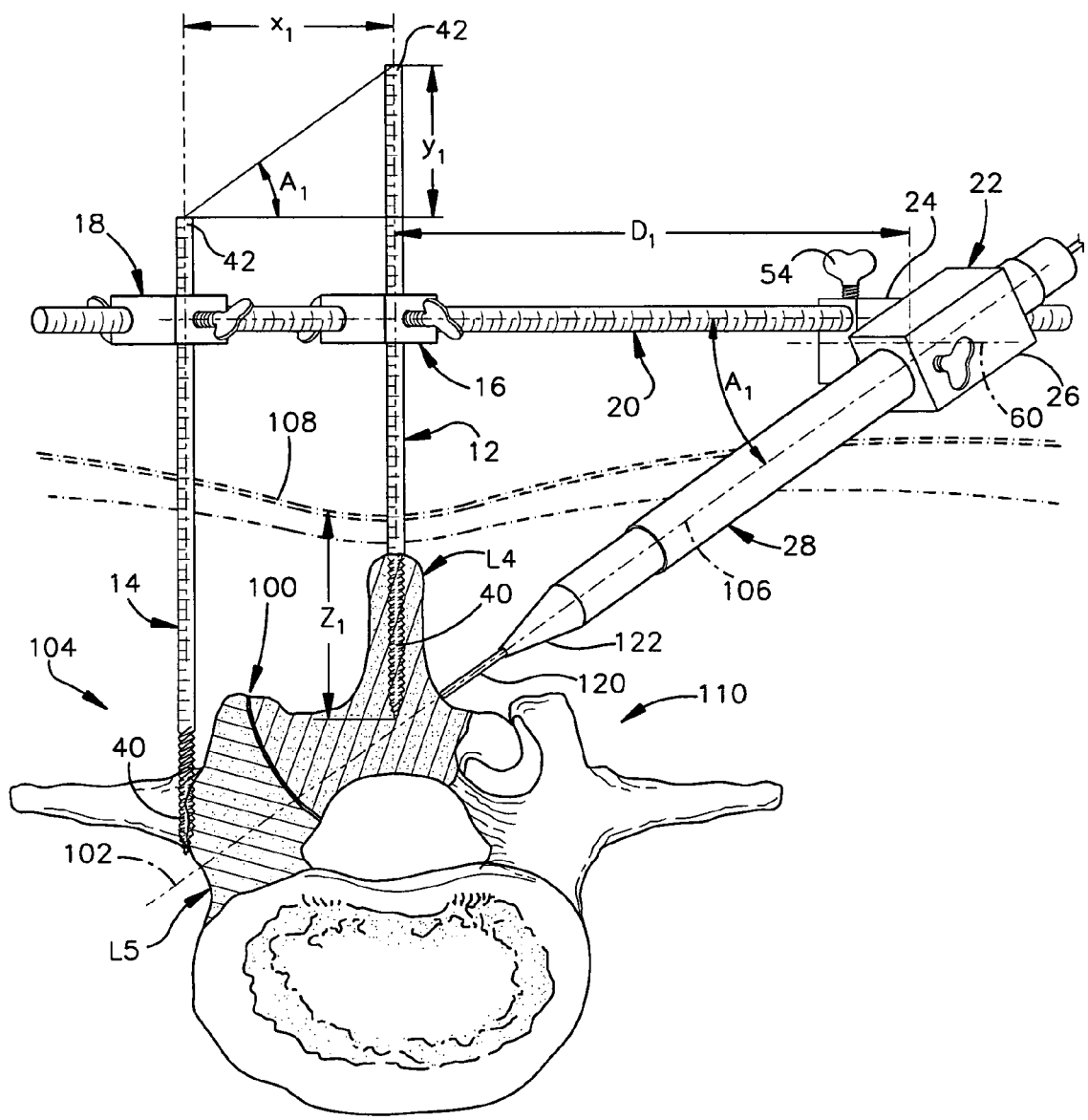
FIG. 7 is a schematic view of adjacent lumbar vertebrae in the transverse plane and illustrating components of the apparatus of FIG. 1 at an early stage of the inventive method for placing a facet screw across a facet joint.

The present invention relates to a minimally invasive method and apparatus for placing facet screws and fusing adjacent vertebrae. As representative of the present invention, FIG. 1 illustrates an apparatus 10 comprising first and second Kirschner wires 12 and 14 (commonly referred to as "K-wires"), first and second fixation blocks 16 and 18, a rod member 20, a swivel block assembly 22 comprising first and second block members 24 and 26, and a cannula 28.

As may be seen in FIG. 3, the rod member 20 is a cylindrical component that may be hollow or solid and is made from any suitable metal or plastic. The rod member 20 has oppositely disposed first and second ends 30 and 32 and an outer diameter of 4 to 7 mm. The rod member 20 includes an outer surface 34 with graduations for measuring axial distances along its length. It is contemplated that other means for measuring axial length along the rod member 20 could also be used.

The first and second K-wires 12 and 14 (FIG. 2) are identical parts, although it should be understood that the K-wires could have different sizes or shapes. Each of the first and second K-wires 12 and 14 is an elongate rod made of a biocompatible metal or other suitable material with an outer diameter of 2 to 4 mm. As shown in FIGS. 2 and 2A, each K-wire 12 and 14 has oppositely disposed distal and proximal ends 40 and 42 and a cylindrical outer surface 44 extending between the ends. The distal end 40 of each of the K-wires 12 and 14 includes self-tapping threads 46. The cylindrical outer surface 44 of each of the K-wires 12 and 14 includes graduations for measuring axial lengths along each K-wire. It is contemplated that other means for measuring axial length along the K-wires 12 and 14 could also be used.

The first and second fixation blocks 16 and 18 (FIGS. 4 and 4A) are also identical components, although it should be understood that certain aspects of the fixation blocks need not be identical. Each of the first and second fixation blocks 16 and 18 is a generally rectangular part made of any suitable metal or plastic. The first fixation block 16 (FIG. 4) includes perpendicularly extending first and second passages 50 and 52. As shown in FIG. 3, the first and second passages 50 and 52 are offset from each other by a predetermined amount and thus do not intersect. In the assembled condition of FIG. 1, the first K-wire 12 extends into the first passage 50 in the first fixation block 16 and the rod member 20 extends into the second passage 52.

The first fixation block 16 further includes threaded fasteners in the form of thumbscrews 54 that extend into the first and second passages 50 and 52 for securing the first K-wire 12 and the rod member 20 in the first and second passages, respectively. It should be understood, however, that other suitable means for securing the first K-wire 12 and the rod member 20 to the first fixation block 16, such as clamps, latches, ratchet mechanisms, etc., could also be used, and that the securing means could be positioned on the exterior of the first fixation block.

In an identical fashion to the first fixation block 16, the second fixation block 18 includes perpendicularly extending first and second passages 56 and 58 that are offset from each other by a predetermined amount and thus do not intersect. The predetermined amount of offset between the first and second passages 56 and 58 in the second fixation block 18 is the same as the predetermined amount of offset between the first and second passages 50 and 52 in the first fixation block 16. In the assembled condition of FIG. 1, the second K-wire 14 extends into the first passage 56 in the second fixation block 18 and the rod member 20 extends into the second passage 58.

The second fixation block 18 further includes threaded fasteners in the form of thumbscrews 54 that extend into the first and second passages 56 and 58 for securing the second K-wire 14 and the rod member 20 in the first and second passages 56 and 58, respectively. It should be understood, however, that other suitable means for securing the second K-wire 14 and the rod member 20 to the second fixation block 18, such as clamps, latches, ratchet mechanisms, etc., could also be used, and that the securing means could be positioned on the exterior of the second fixation block.

As shown in FIG. 5, the first and second block members 24 and 26 of the swivel block assembly 22 are movable relative to each other about an axis 60. Each of the first and second block members 24 and 26 is a generally rectangular part made of any suitable metal or plastic. The first block member 24 includes a passage 62 for receiving the rod member 20. A threaded fastener in the form of a thumbscrew 54 extends into the passage 62 for securing the rod member 20 in the passage. The second block member 26 further includes a passage 64 for receiving the cannula 28. A threaded fastener in the form of a thumbscrew 54 extends into the passage 64 for securing the cannula 28 in the passage. It should be understood, however, that other suitable means for securing the rod member 20 and the cannula 28 to the swivel block assembly 22, such as clamps, latches, ratchet mechanisms, etc., could also be used, and that these securing means could be positioned on the exterior of the swivel block assembly.

The first and second block members 24 and 26 further include abutting surfaces 66 and 68, respectively, with means for controllably adjusting the angular position of the block members relative to each other. In accordance with the illustrated embodiment of the invention, this is accomplished via a first ring of radially extending serrations 70 on the surface 66 of the first block member 24 that is centered on the axis 60 and engaged with a second ring of radially extending serrations 72 on the surface 68 of the second block member 26 that is also centered on the axis 60. A threaded fastener in the form of a thumbscrew 74 extends through the first block member 24 and into a threaded opening 76 in the second block member 26 along the axis 60 for securing the block members in a desired relative angular position. It should be understood, however, that other suitable means for securing the block members 24 and 26 in a desired angular position could be used, and that the securing means could be located elsewhere on the block members. Further, it should also be understood that other suitable means for controllably adjusting the relative angular position of the first and second block members 24 and 26 could be employed.

The cannula 28 (FIG. 1) is a thin-walled hollow cylinder made of a biocompatible metal or other suitable material and has oppositely disposed distal and proximal ends 80 and 82. In accordance with one embodiment of the present invention, the cannula 28 has an outer diameter of about 4.5 mm and an inner diameter of about 4.3 mm, although it should be understood that these dimensions may be varied between 4 and 6 mm for the outer diameter and 3.5 to 5 mm for the inner diameter.

FIG. 6 illustrates a screw 84 to be implanted in accordance with the present invention. The screw 84 is a self-tapping facet screw made of a biocompatible material, such as titanium. As illustrated in FIG. 6, the screw 84 has a head 86 with a triangular-shaped receptacle 88. In accordance with one embodiment, the screw has a major diameter of 4.3 mm and a minor diameter of 3.8 mm, but it should be understood that these dimensions can be varied based on the pathology and surgical needs. The length L of the screw 84 is determined during surgery as discussed below.

Figure 8:
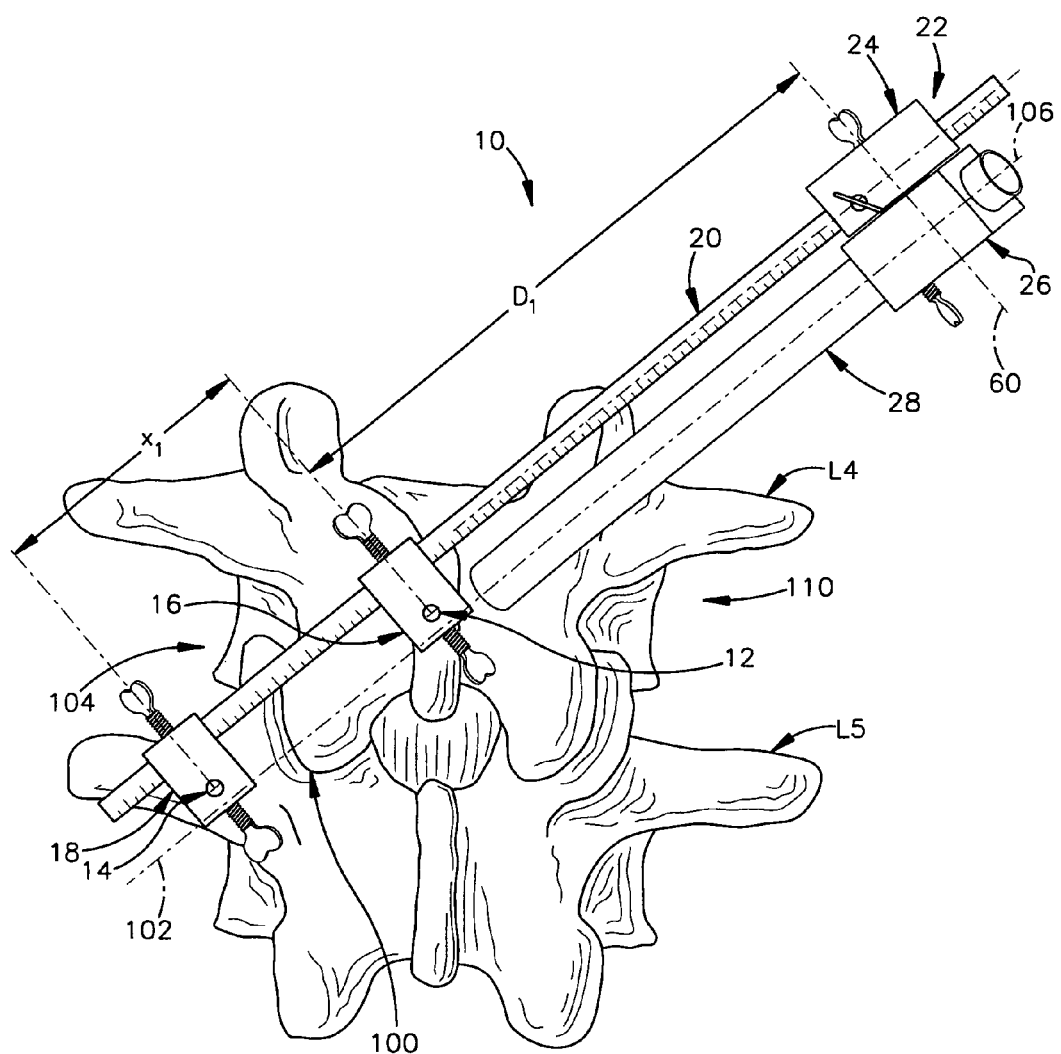
FIG. 8 is a schematic posterior view of the apparatus at a subsequent stage to that of FIG. 7.
Figure 9:
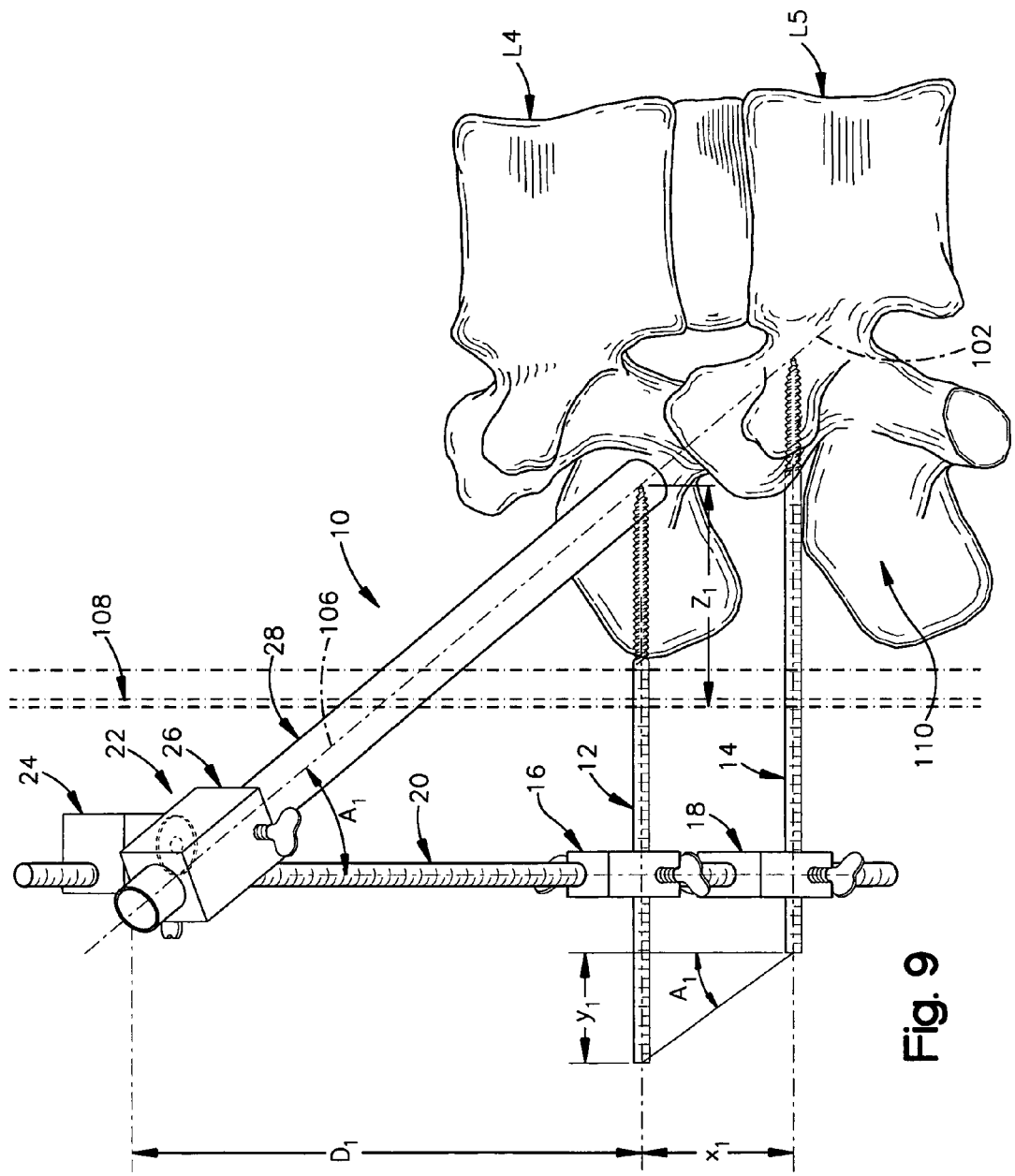
FIG. 9 is a schematic side view of FIG. 8.

To use the apparatus 10 to place the facet screw 84 across a first facet joint 100 between adjacent vertebrae, such as the L4 and L5 vertebrae shown in FIGS. 7-9, in a minimally invasive procedure, the patient is placed in the prone position and X-ray imaging equipment is set-up to provide views in both the antero-posterior (AP) plane and the lateral plane so that the procedure can be performed under fluoroscopic guidance. It should be understood to those skilled in the art that other known navigation assistance devices and equipment could alternatively be used. A stab incision is then made through the skin and the first K-wire 12 is inserted through the incision and into the center of the spinous process of the L4 vertebrae. As may be seen in FIGS. 7 and 9, the distal end 40 of the first K-wire 12 is screwed into the spinous process until the distal tip reaches a point along a first axis 102 on which a first screw 84 is to be inserted.

Next, through another percutaneous stab incision, the second K-wire 14 is inserted into the transverse process on a first side 104 (the left side as viewed in FIG. 7) of the L5 vertebrae and extends in parallel with the first K-wire 12 in both the sagittal and coronal planes as shown in FIGS. 7-9. The distal end 40 of the second K-wire 12 is screwed into the transverse process just lateral to the facet joint 100 on the first side 104 of the vertebrae up to the junction of the transverse process and the pedicle on the first side.

The first fixation block 16 is then slid onto the first K-wire 12 with the first K-wire extending into the first passage 50 in the first fixation block. Similarly, the second fixation block 18 is slid onto the second K-wire 14 with the second K-wire extending into the first passage 56 in the second fixation block. The first end 30 of the rod member 20 is slid then into the second passages 52 and 58 in the first and second fixation blocks 16 and 18, respectively, so that it extends across the first and second K-wires 12 and 14. The thumbscrews 54 that extend into the second passages 52 and 58 are tightened to secure the rod member 20 to the fixation blocks 16 and 18.

According to the inventive method, the next steps involve calculations to determine the following three parameters: (1) the length $L_1$ of the screw 84 to be implanted; (2) the desired angle $A_1$ for the cannula 28 to extend from the swivel block assembly 22, which provides the trajectory for the implantation of a first screw 84 across the facet joint 100 on the first side 104; and (3) the desired axial position $D_1$ for the swivel block assembly 22 along the rod member 20. As will be seen in the calculations set forth below, the apparatus 10 according to the present invention utilizes the position and relationship of the first and second K-wires 12 and 14 to determine the entry point and trajectory upon which the screw 84 is implanted into the L4 and L5 vertebrae.

The screw length $L_1$ is determined by measuring the axial difference $X_1$ between the two identical K-wires 12 and 14 and measuring the horizontal difference $Y_1$ between the two K-wires. The graduations on the K-wires 12 and 14 and/or another suitable means can assist in taking these measurements. The screw length $L_1$ is calculated with the following equation: $L_1=\sqrt{(X_1^2+Y_1^2)}$. Use of this equation to determine the desired screw length $L_1$ helps to ensure that the screw 84, when implanted across the facet joint 100, will not extend beyond the cortex of the superior articular process where nerve damage could become an issue.

The desired angle $A_1$ for the cannula 28 to extend from the swivel block assembly 22, which provides the trajectory for the implantation of the first screw 84 across the facet joint 100 on the first side 104, is calculated based on the measured X and Y values and the angle between these distances using the following equation: $A_1=\tan^{-1}(Y_1/X_1)$. As shown in FIG. 5, the calculated angle $A_1$ between the proximal ends 42 of the K-wires 12 and 14 also defines the angle ($A_1$) between the centerline of the rod member 20 and the centerline 108 of the second passage 64 through the second block member 26. The centerline 106 of the passage 64 is also the centerline of the cannula 28 and is co-linear with the screw trajectory axis 102, as may be seen in FIG. 7. The second block member 26 is then rotated about the axis 60 relative to the first block member 24 to set the desired angle $A_1$ for the centerline 106 of the cannula 28, which extends from the second block member. At the desired angle $A_1$, the first and second rings of serrations 70 and 72 on the first and second block members 24 and 26, respectively, are brought into engagement and secured by the thumbscrew 74 to ensure that the relative angular position of the block members is fixed. It should be understood by those skilled in the art that other means, such as an angle measuring device, for determining the desired angle $A_1$ could also be used in conjunction with the distances $X_1$ and $Y_1$ between the K-wires 12 and 14.

The axial position, or distance, $D_1$ for the swivel block assembly 22 on the rod member 20 is calculated by first measuring the distance $Z_1$ of penetration of the first K-wire 12 (i.e., the distance $Z_1$ extends between the distal tip of the first K-wire and the skin 108) using the graduations on the first K-wire. The distance $D_1$ is then calculated with the following equation: $D_1=(X_1/Y_1)Z_1$. The distance $D_1$ for the swivel block assembly 22 along the rod member 20 is measured from the centerline of the first K-wire 12 to the axis 60 of the swivel block assembly. The graduations on the rod member 20 or another suitable means can be used for setting the swivel block assembly 22 at the desired axial position.

Next, the swivel block assembly 22 is slid onto the second end 32 of the rod member 20, which is projecting out over a second side 110 (or right side as viewed in FIG. 7) of the L4 and L5 vertebrae, with the rod member 20 extending through the passage 62 in the first block member 24. The thumbscrew 54 is used to secure the swivel block assembly 22 at the calculated desired axial position $D_1$ on the rod member 20.

The rod member 20 and the swivel block assembly 22 are then lowered to a height above the skin 108 that provides sufficient clearance for the swivel block assembly as shown in FIG. 7. Finally, the first and second fixation blocks 16 and 18 are secured to the first and the second K-wires 12 and 14, respectively, with the thumbscrews 54. The apparatus 10 is now in position for the first screw 84 to be placed across the facet joint 100 on the first side 104 of the L4 and L5 vertebrae.

A scalpel (not shown) is used to incise the skin 108 on the second side 110 of the vertebrae to accept the cannula 28. With the cannula 28 temporarily removed, the incision is made using the passage 64 through the second block member 24 of the swivel block assembly 22 to orient the incision along the proper axes 102 and 106. Under fluoroscopic guidance, a guidewire 120 is passed through the incision along the axes 102 and 106 to the starting point for the screw 84 which is located adjacent the junction of the spinous process and the lamina as shown in FIG. 7. It is contemplated that a Jamshidi needle or other suitable instrument could be used in place of the guidewire 120.

Next, a blunt obturator 122 is passed over the guidewire 120 to create subcutaneous space for the cannula 28 along the axis 102. The cannula 28, which is guided for movement along the axes 102 and 106 by virtue of the passage 64 through the second block member 26, is then passed over the obturator 122 and the guidewire 120. The cannula 28 is moved along the axes 102 and 106 until the distal end of the cannula docks against the lamina on the second side 110 of the L4 vertebrae as shown in FIGS. 8 and 9. The guidewire 120 and the obturator 122 are then removed from the cannula 28. At this point in the procedure, a small (e.g., 2 mm) diameter scope may be passed down the cannula 28 to inspect the anatomy and the condition of the vertebrae.

Figure 10:
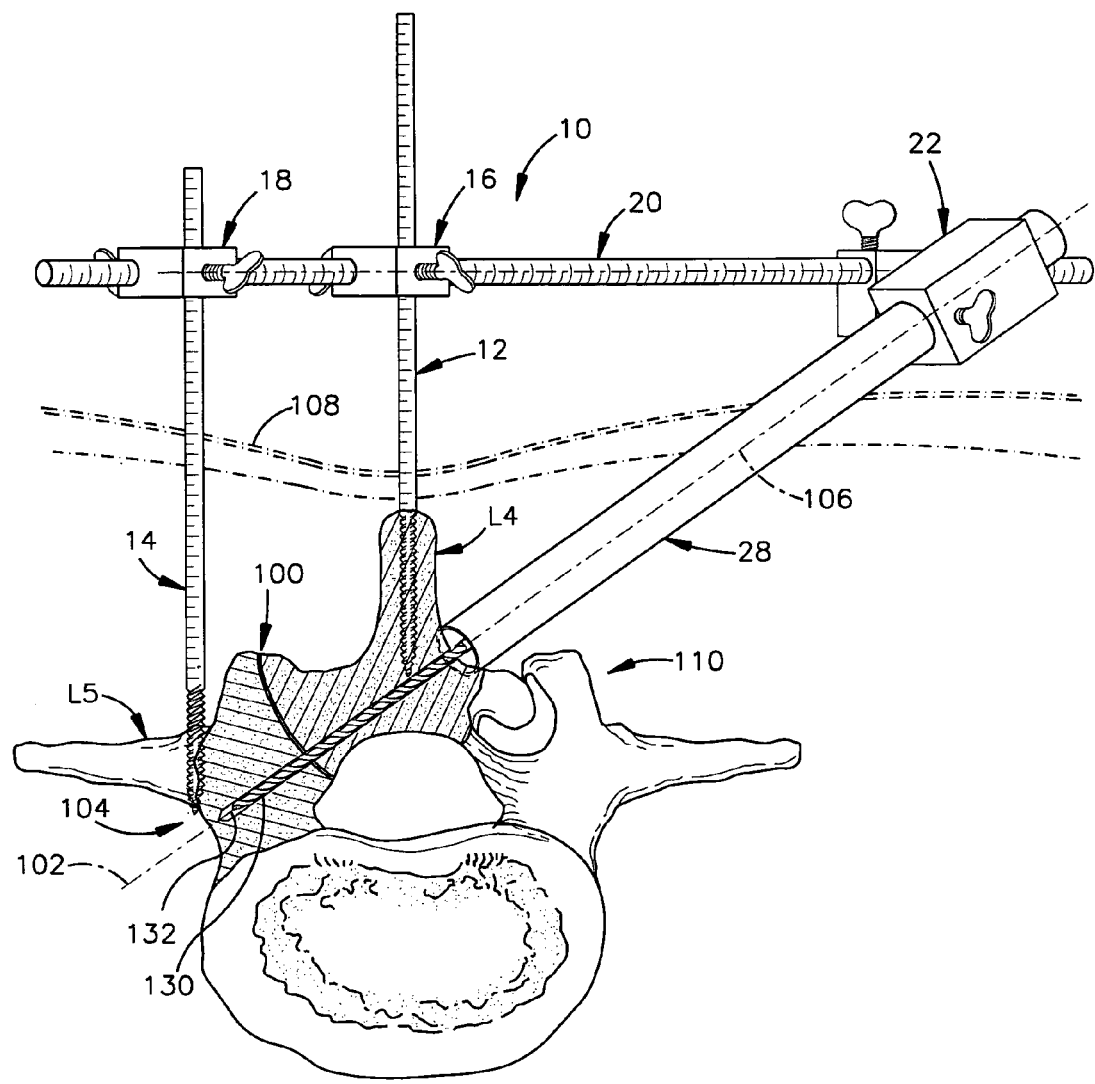
FIGS. 10-12 are views similar to FIG. 7 illustrating various steps according to the inventive method.

After ensuring that all of the thumbscrews 54 and 74 are secure and that the alignment of the axis 102 is correct, a drill bit 130 (FIG. 10) is inserted into the cannula 28. The drill bit 130 is rotated by a drill (not shown) to drill a pilot hole 132 along the axis 102 through the lamina on the second side 110 of the L4 vertebrae, through the inferior articular process on the first side 104 of the L4 vertebrae, across the facet joint 100 on the first side, and into the superior articular process of the L5 vertebrae. It is contemplated that a drill guide (not shown) could be used to center the drill bit 130 in the cannula 28 and ensure that the pilot hole 132 extends along the axis 102.

Figure 11:
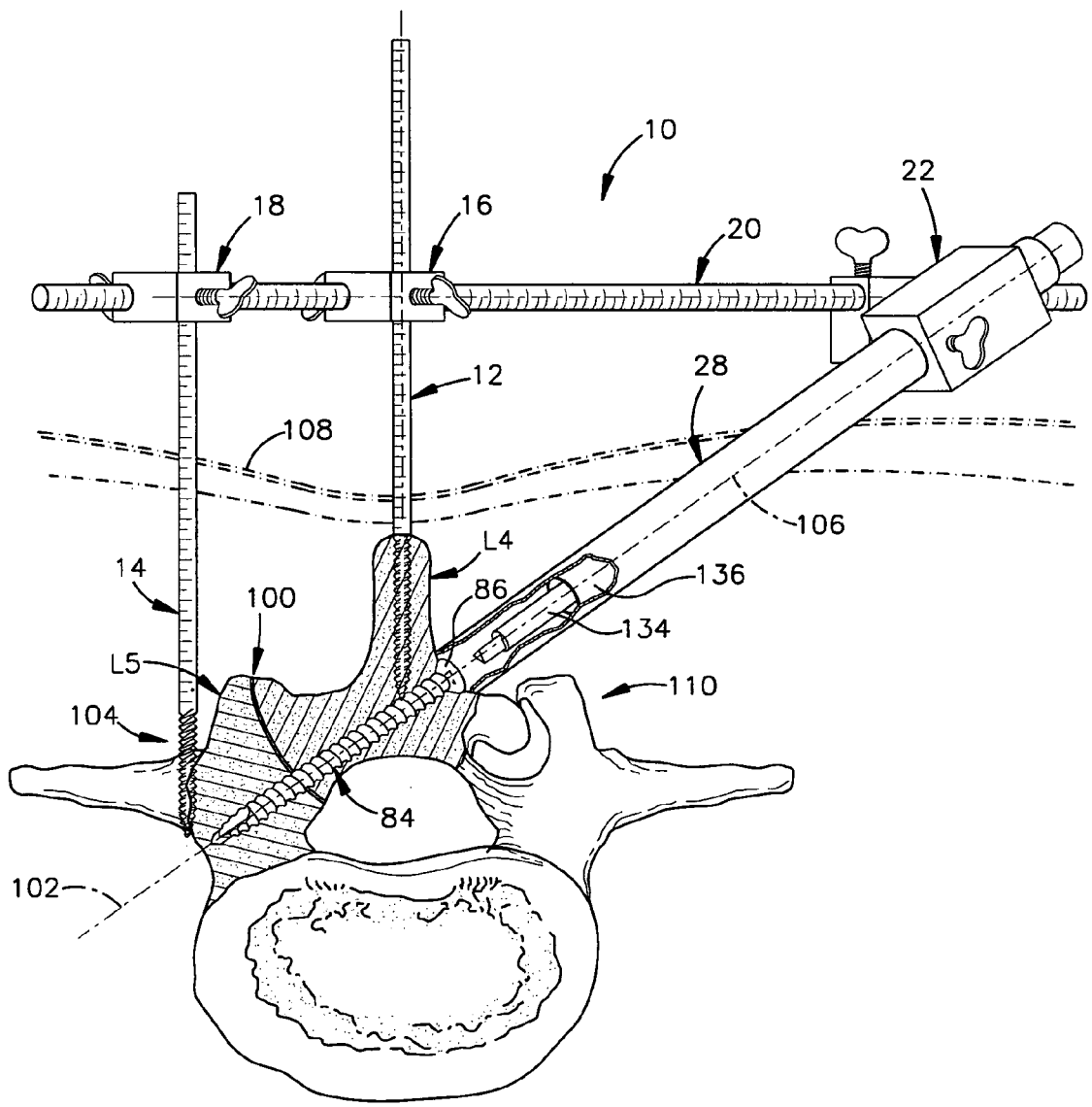

As shown in FIG. 11, the self-tapping screw 84 is then inserted into the cannula 28 and screwed into the pilot hole 132 using a driver 134. In the illustrated embodiment, the head 86 of the screw 84 has a maximum outer diameter that matches the inner diameter of a second cannula 136 that is inserted into the cannula 28 to aid in keeping the screw aligned on the axis 102 during implantation. Further, the illustrated driver 134 has a triangular tip for receipt in the receptacle 88 of the screw 84, although it should be understood that the receptacle and the corresponding driver tip could utilize a different geometry. The screw 84 is advanced until the head 86 seats against the lamina on the second side 110 of the L4 vertebrae. Fluoroscopic guidance coupled with the aforementioned calculation to select the length $L_1$ of the screw 84 ensures that the distal tip of the screw does not penetrate beyond the cortex of the L5 vertebrae. As implanted, the screw 84 extends across the facet joint 100 to connect the inferior articular process of the L4 vertebrae to the superior articular process of the L5 vertebrae.

With the first screw 84 implanted, the cannula 28 is removed from the skin 108 and the thumbscrew 74 is released to allow relative movement of the first and second block members 24 and 26. The second block member 26 is then swiveled to aim the centerline 106 of the cannula 28 along a second axis 140 (FIG. 13) that extends toward a facet joint 142 (FIG. 12) on the second side 110 of the vertebrae. In order to aim the cannula 28 toward the facet joint 142, the other thumbscrews 54 may also be released to allow additional movement of the swivel block assembly 22. Releasing the other thumbscrews 22 may allow the cannula 28 to be positioned over the existing incision through the skin 108 while being aimed toward the facet joint 142 along the axis 140 so that the same incision can be utilized again.

Figure 12:
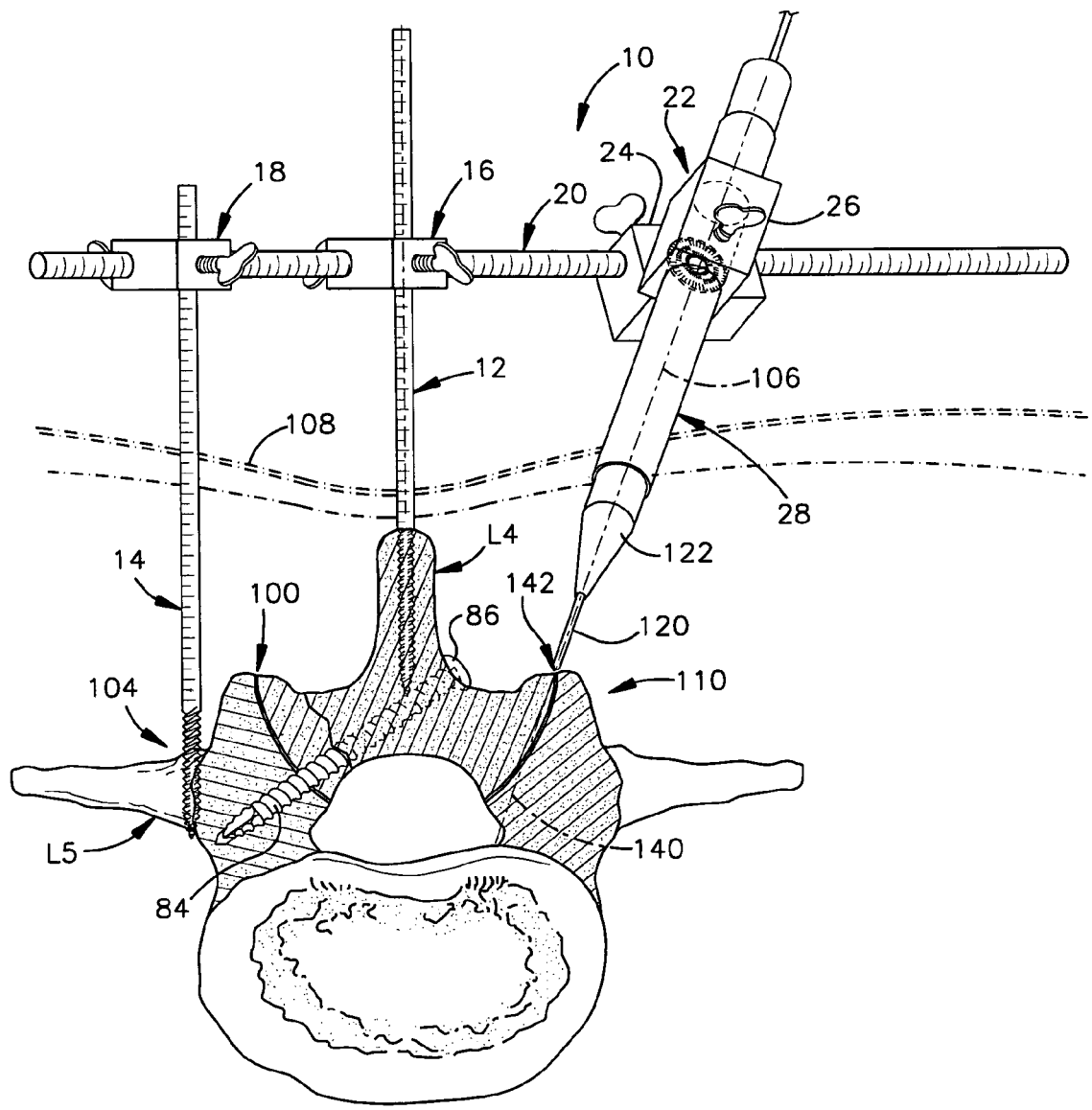
Figure 13:
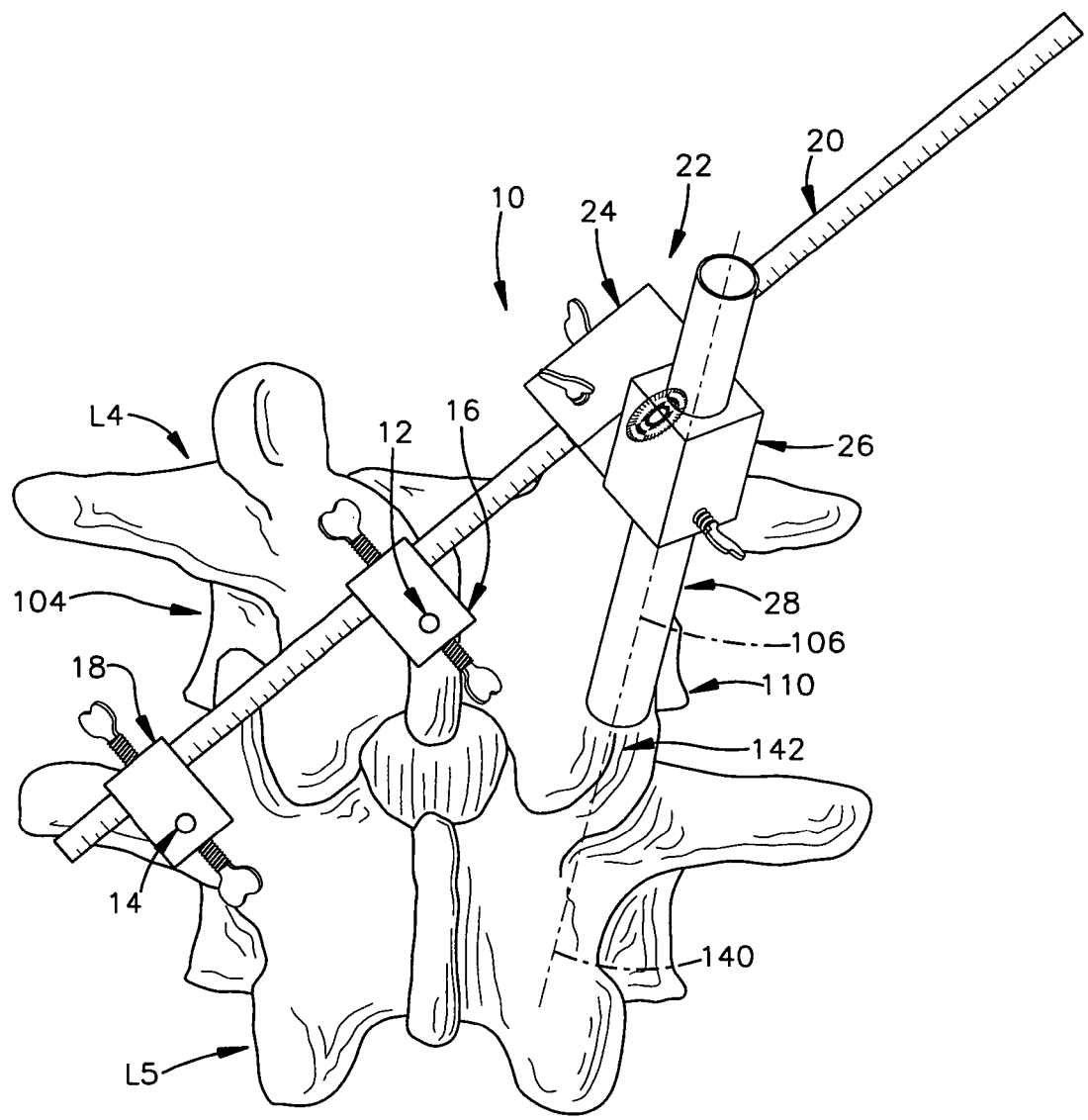
FIG. 13 is a schematic posterior view of the apparatus.
Figure 14:
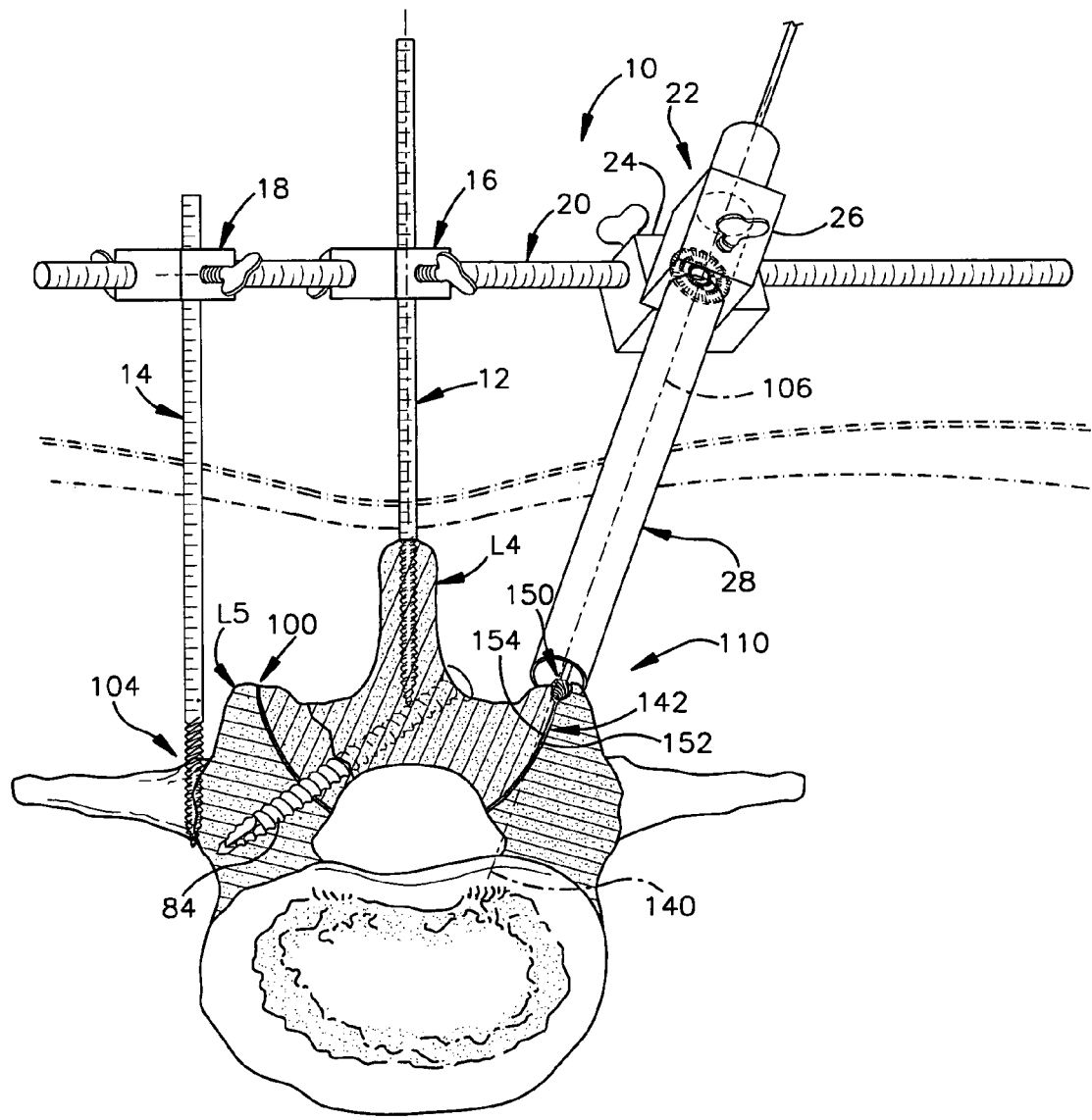
FIGS. 14 and 15 are views similar to FIG. 12 illustrating additional steps according to the inventive method.

After tightening all of the thumbscrews 54 and 74 to secure the components of the apparatus 10 in the positions shown in FIG. 12, the guidewire 120 (or Jamshidi needle, etc.) is passed through the incision along the axis 140 to the surface of the facet joint 142 on the second side 110 of the L4 and L5 vertebrae under fluoroscopic guidance. Next, the blunt obturator 122 is passed over the guidewire 120 to create subcutaneous space for the cannula 28 along the axis 140. The cannula 28, which is guided for movement along the axes 140 and 106 by virtue of the passage 64 through the second block member 26, is then passed over the obturator 122 and the guidewire 120. The cannula 28 is moved along the axes 140 and 106 until the distal end of the cannula 28 docks against the surface of the facet joint 142 as shown in FIGS. 13 and 14. The guidewire 120 and the obturator 122 are then removed from the cannula 28.

After ensuring that all of the thumbscrews 54 and 74 are secure and that the alignment of the axis 140 is correct, a burring bit 150 (FIG. 14) is inserted into the cannula. The burring bit 150 is rotated by a drill (not shown) to burr the opposing surfaces 152 and 154 of the inferior articular process and the superior articular process on the second side 110 of the L4 and L5 vertebrae, respectively. Burring these surfaces 152 and 154 widens the facet joint so that a bone graft material is more easily placed into the facet joint 142. It is contemplated that the cannula 28 may be moved slightly along the facet joint 142 during the burring process in order to access a larger area of the facet joint with the burring bit 150.

Figure 15:
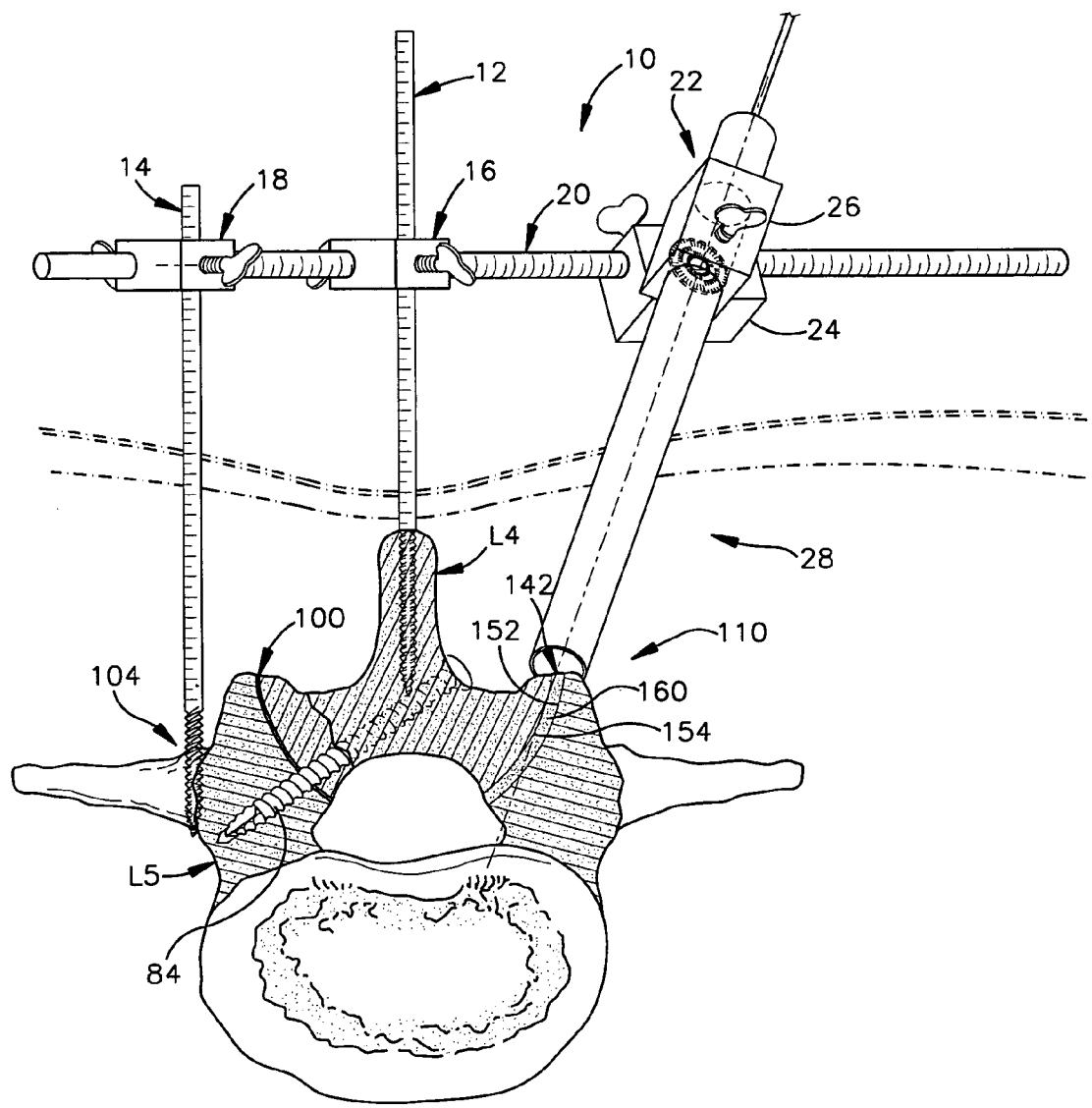

After the articular surfaces 152 and 154 of the facet joint 142 on the second side 110 of the L4 and L5 vertebrae have been burred out, a bone graft (or bone substitute) material 160 (FIG. 15) for helping to fuse the L4 and L5 vertebrae is placed into the facet joint 142 through the cannula 28. The bone graft material 160 may be fed into the facet joint 142 using any known suitable instrument(s). The cannula 28 is then removed from the incision on the second side 110 of the vertebrae.

Figure 16:
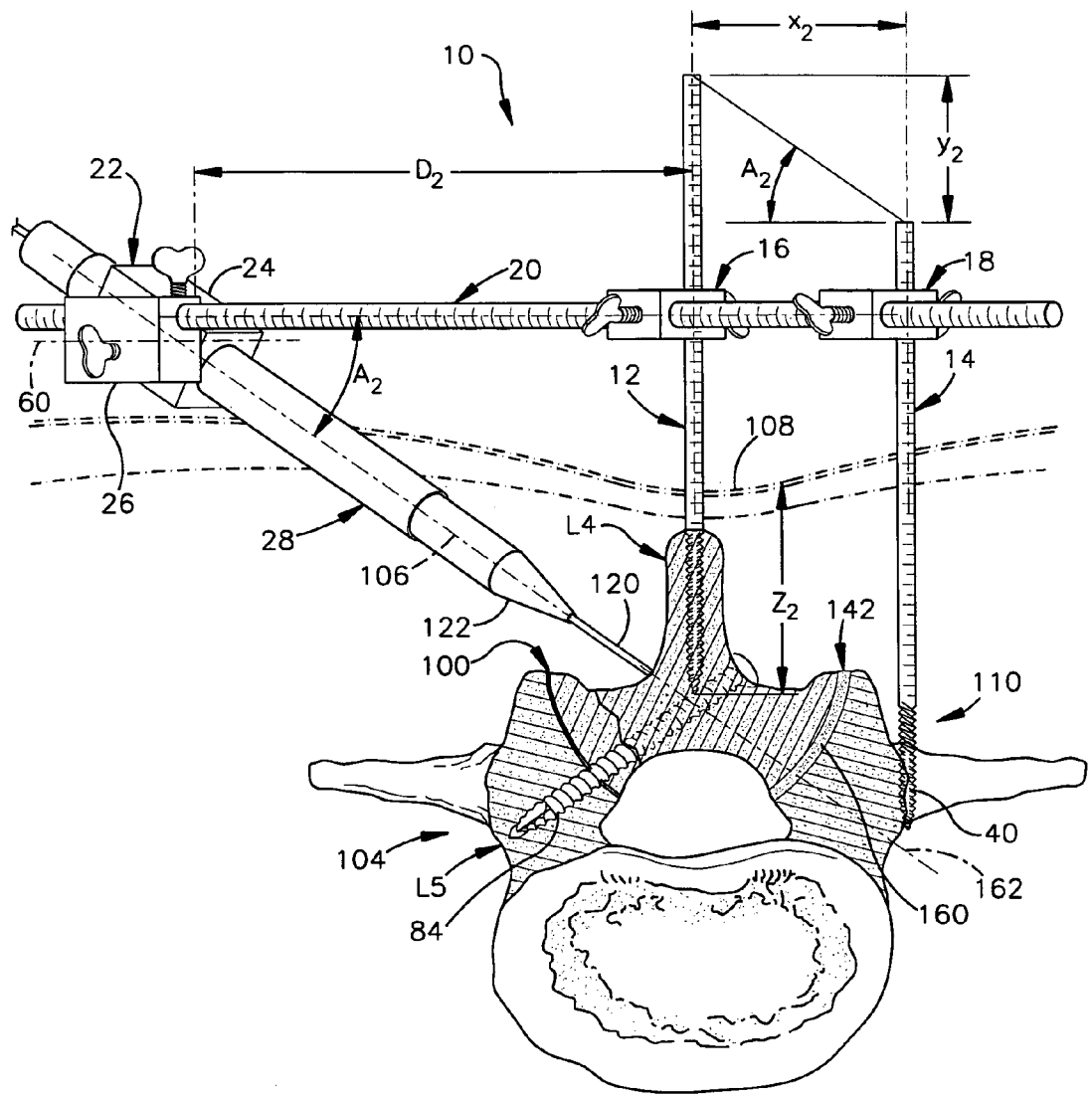
FIG. 16 is a view similar to FIG. 15 illustrating components of the apparatus of FIG. 1 in different positions for placing a facet screw across a facet joint on the opposite side.
Figure 17:
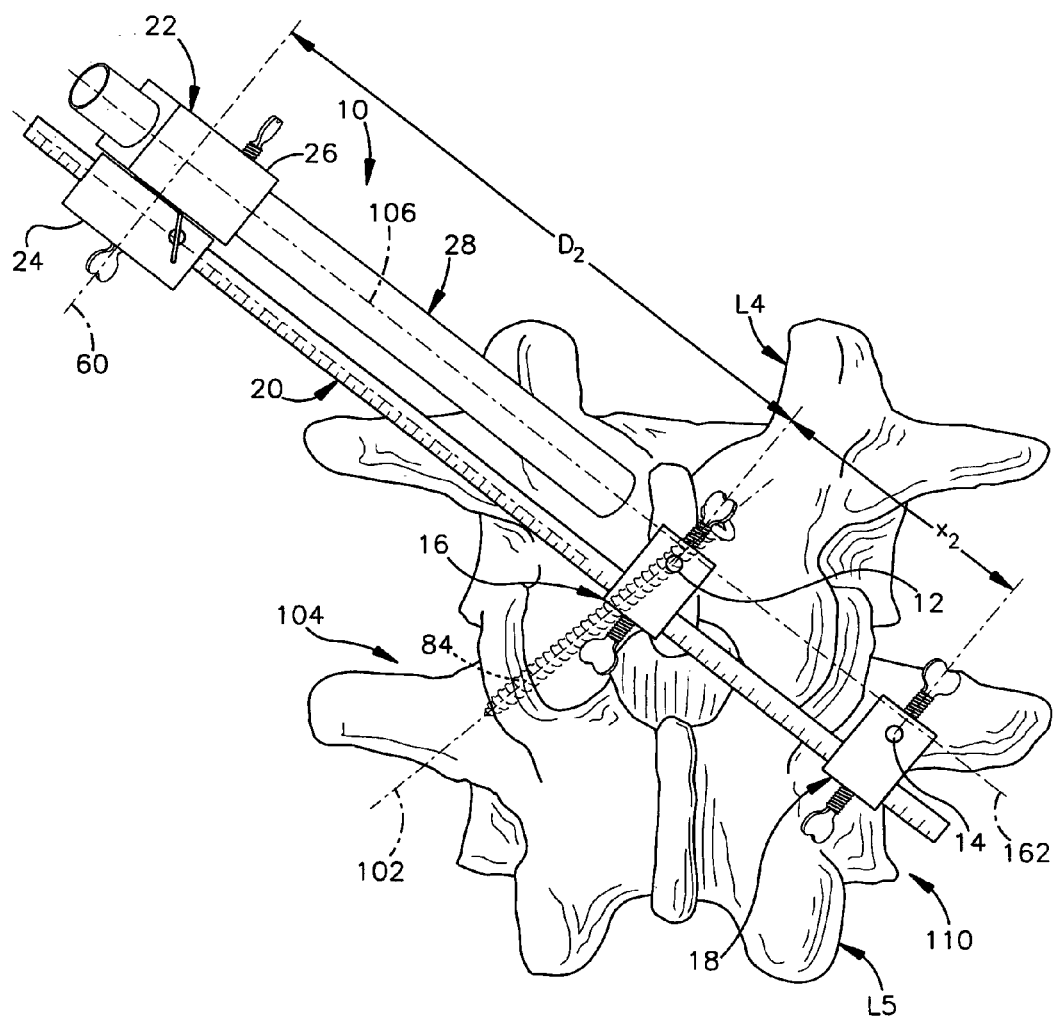
FIG. 17 is a schematic posterior view of the apparatus at a subsequent stage to that of FIG. 16.
Figure 18:
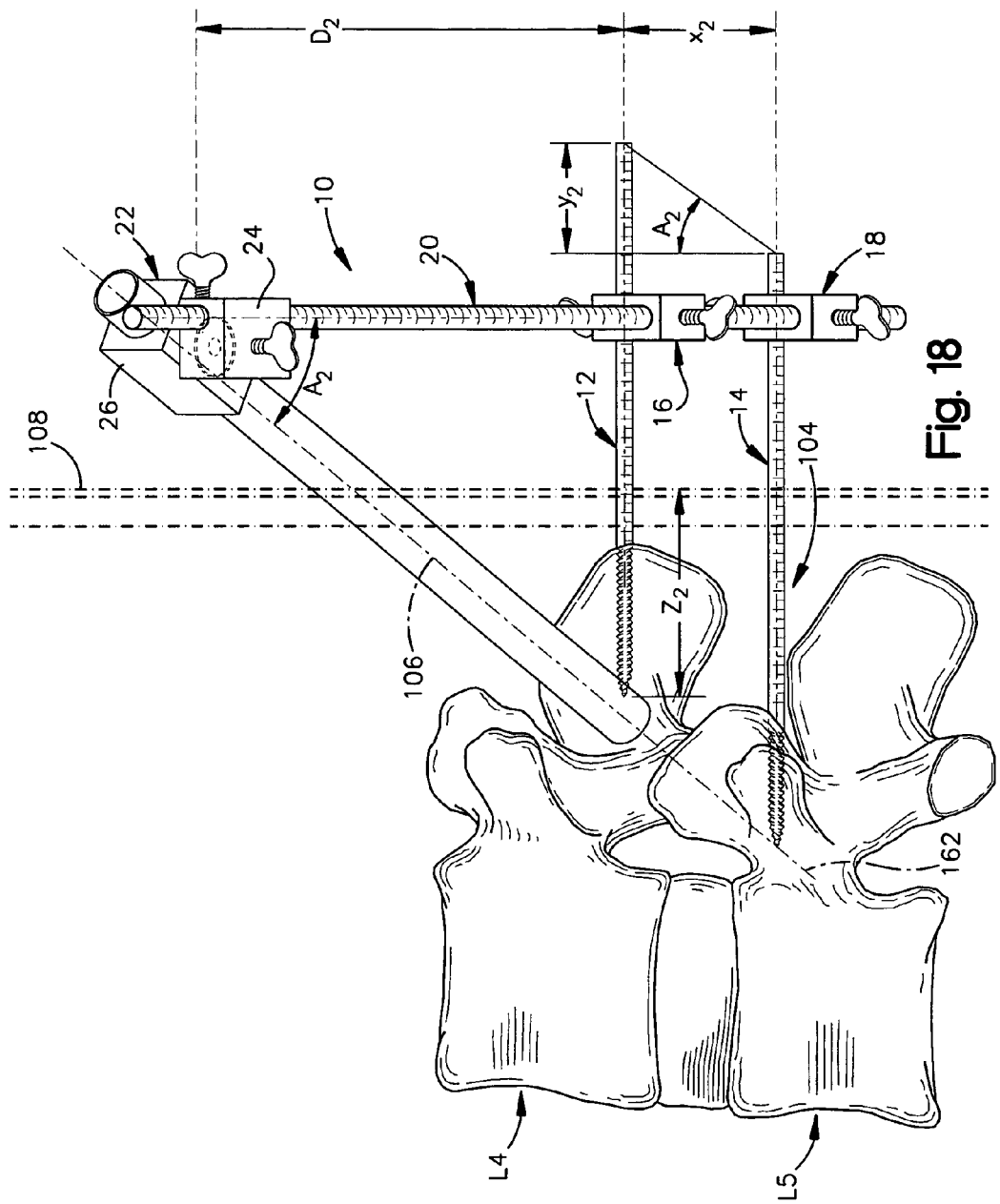
FIG. 18 is a schematic side view of the opposite side shown in FIG. 17.

The next steps in the process are to loosen all of the thumbscrews 54 and 74, remove the fixation blocks 16 and 18 from the K-wires 12 and 14, and disassemble the swivel block assembly 22 from the rod member 20. The second K-wire 14 is then removed from the transverse process on the first side 104 of the L5 vertebrae. Next, through another percutaneous stab incision, the second K-wire 14 is inserted into the transverse process on the second side 110 of the L5 vertebrae so that it again extends in parallel with the first K-wire 12 in both the sagittal and coronal planes as shown in FIGS. 16-18. The distal end 40 of the second K-wire 14 is screwed into the transverse process just lateral to the facet joint 142 on the second side 110 of the vertebrae up to the junction of the transverse process and the pedicle.

The first fixation block 16 is then slid onto the first K-wire 12 with the first K-wire extending into the first passage 50 in the first fixation block. Similarly, the second fixation block 18 is slid onto the second K-wire 14 with the second K-wire extending into the first passage 56 in the second fixation block. The first end 30 of the rod member 20 is slid then into the second passages 52 and 58 in the first and second fixation blocks 16 and 18, respectively, so that it extends across the first and second K-wires 12 and 14. The thumbscrews 54 that extend into the second passages 52 and 58 are tightened to secure the rod member 20 to the fixation blocks 16 and 18.

Once again, the next steps in the process involve calculations to determine the following three parameters: (1) the length $L_2$ of a second screw 84 to be implanted; (2) the desired angle $A_2$ for the cannula 28 to extend from the swivel block assembly, which provides a trajectory axis 162 for the implantation of the second screw 84 across the facet joint 142 on the second side 110; and (3) the desired axial position $D_2$ for the swivel block assembly 22 along the rod member 20. As mentioned above, the apparatus 10 according to the present invention utilizes the position and relationship of the first and second K-wires 12 and 14 to determine the entry point and trajectory upon which the second screw 84 is implanted into the L4 and L5 vertebrae.

The screw length $L_2$ is determined by measuring the axial difference $X_2$ between the two identical K-wires 12 and 14 and measuring the horizontal difference $Y_2$ between the two K-wires. The graduations on the K-wires 12 and 14 or another suitable means can assist in taking these measurements. The screw length $L_2$ is then calculated with the following equation: $L_2=\sqrt{(X_2^2+Y_2^2)}$. Use of this equation to determine the desired screw length $L_2$ helps to ensure that the second screw 84, when implanted across the facet joint 142, will not extend beyond the cortex of the superior articular process where nerve damage could become an issue. It should be noted that in many cases, the lengths for the first and second screws 84 will likely be the same.

The desired angle $A_2$ for the cannula 28 to extend from the swivel block assembly 22, which provides the trajectory for the implantation of the second screw 84 across the facet joint 142 on the second side 110, is calculated with the following equation: $A_2=\tan^{-1}(Y_2/X_2)$. As shown in FIG. 16, the calculated desired angle $A_2$ between the proximal ends 42 of the K-wires 12 and 14 also defines the angle ($A_2$) between the centerline of the rod member 20 and the centerline 106 of the second passage 64 through the second block member 26. The centerline of the passage 64 is also the centerline of the cannula 162, as may be seen in FIG. 16. The second block member 26 is then rotated about the axis 60 relative to the first block member 24 to set the desired angle $A_2$ for the centerline 106 of the cannula 28, which extends from the second block member. At the desired angle $A_2$, the first and second rings of serrations 70 and 72 on the first and second block members 24 and 26, respectively are brought into engagement and secured by the thumbscrew 74 to ensure that the relative angular position of the block members is fixed. It should be understood by those skilled in the art that other means, such as an angle measuring device, for determining the desired angle $A_2$ could also be used in conjunction with the distances $X_2$ and $Y_2$ between the K-wires 12 and 14.

The axial position, or distance, $D_2$ for the swivel block assembly 22 on the rod member 20 is calculated by first measuring the distance $Z_2$ of penetration of the first K-wire 12 (i.e., the distance $Z_2$ extends between the distal tip of the first K-wire and the skin 108) using the graduations on the first K-wire. The distance $D_2$ is then calculated with the following equation: $D_2=(X_2/Y_2)Z_2$. The distance $D_2$ for the swivel block assembly 22 along the rod member 20 is measured from the centerline of the first K-wire 12 to the axis 60 of the swivel block assembly 22. The graduations on the rod member 20 or another suitable means can be used for setting the swivel block assembly 22 at the desired axial position.

Next, the swivel block assembly 22 is then slid onto the second end 32 of the rod member 20, which is projecting out over the first side 104 of the vertebrae, with the rod member extending through the passage 62 in the first block member 24. The thumbscrew 54 is used to secure the swivel block assembly 22 at the calculated desired axial position $D_2$ on the rod member 20.

The rod member 20 and the swivel block assembly 22 are then lowered to a height above the skin 108 that provides sufficient clearance for the swivel block assembly as shown in FIG. 16. Finally, the first and second fixation blocks 16 and 18 are secured to the first and second K-wires 12 and 14, respectively, with the thumbscrews. The apparatus 10 is now in position for the second screw 84 to be placed across the facet joint 142 on the second side 110 of the vertebrae. It is important to note at this point that the predetermined offset between the first and second passages 50 and 52 in the first fixation blocks 16 and the first and second passages 56 and 58 in the second fixation block 18 positions the rod member 20 and the swivel block assembly 22 so that the axis 162 for implantation of the second screw 84 is offset from the axis 102 on which the first screw 84 was implanted. This offset ensures that the second screw 84 does not intersect with the first screw 84 as it extends through the spinous process of the L4 vertebrae.

The scalpel (not shown) is used to incise the skin 108 on the first side 104 of the vertebrae to accept the cannula 28. With the cannula 28 temporarily removed, the incision is made using the passage 64 through the second block member 24 of the swivel block assembly 22 to orient the incision on the axes 106 and 162. Under fluoroscopic guidance, the guidewire 120 is passed through the incision along the axes 106 and 162 to the starting point for the screw 84 which is located adjacent the junction of the spinous process and the lamina as shown in FIG. 16. As discussed above, it is contemplated that a Jamshidi needle or other suitable instrument could be used in place of the guidewire 120.

Next, the blunt obturator 122 is passed over the guidewire 120 to create subcutaneous space for the cannula 28 along the axis 162. The cannula 28, which is guided for movement along the axes 106 and 162 by virtue of the passage 64 through the second block member 26, is then passed over the obturator 122 and the guidewire 120. The cannula 28 is moved along the axes 106 and 162 until the distal end of the cannula docks against the lamina on the first side 104 of the L4 vertebrae as shown in FIGS. 17 and 18. The guidewire 120 and the obturator 122 are then removed from the cannula 28. At this point in the procedure, the small diameter scope may again be passed down the cannula 28 to inspect the anatomy and the condition of the vertebrae.

Figure 19:
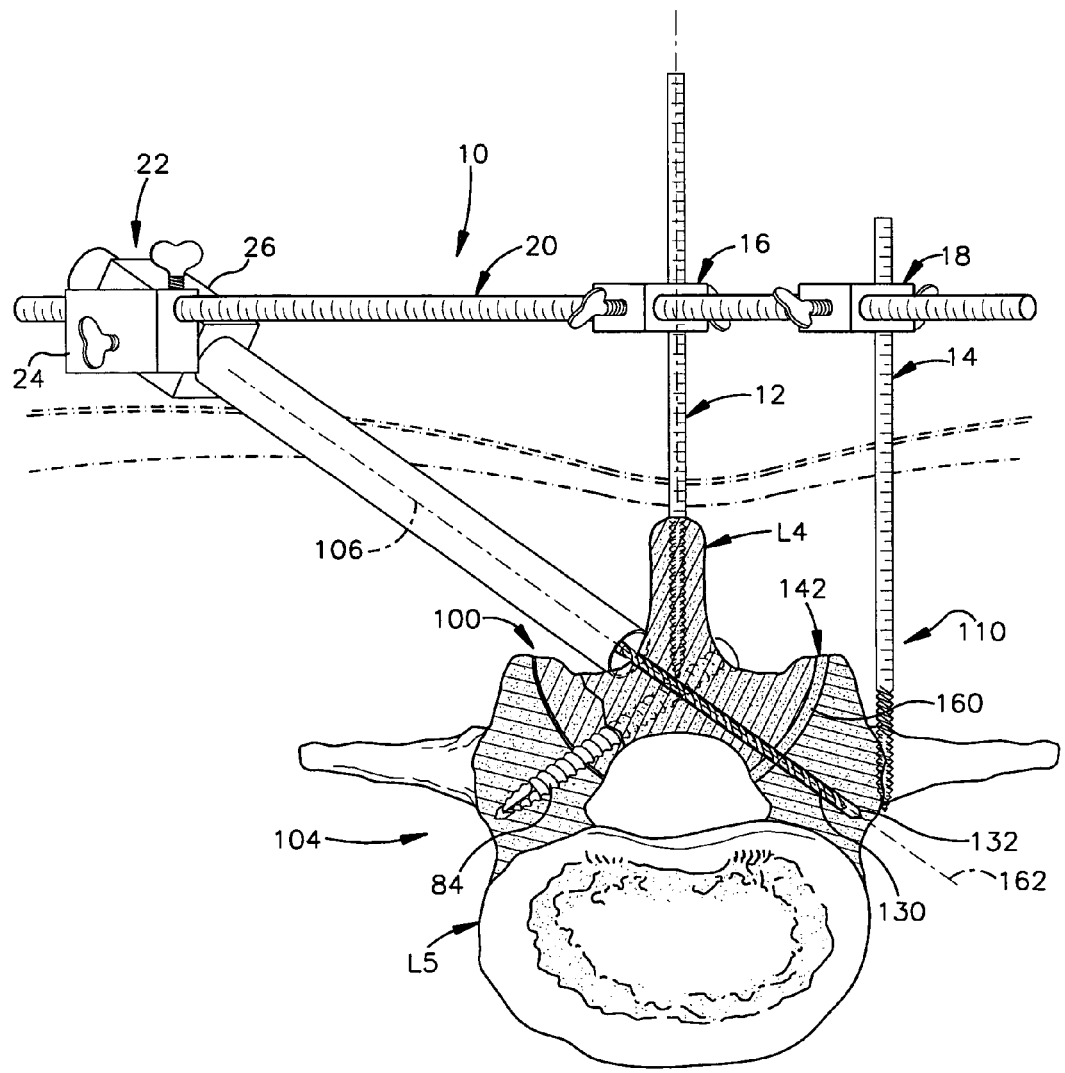
FIGS. 19-21 are views similar to FIG. 16 illustrating various steps according to the inventive method.

After ensuring that all of the thumbscrews 54 and 74 are secure and that the alignment of the axis 162 is correct, the drill bit (FIG. 19) is inserted into the cannula 28. The drill bit 130 is rotated by a drill (not shown) to drill a pilot hole 132 along the axis 162 through the lamina on the first side 104 of the L4 vertebrae, through the inferior articular process on the second side 110 of the L4 vertebrae, across the facet joint 142 and the bone graft material 160 therein, and into the superior articular process of the L5 vertebrae. It is contemplated that a drill guide (not shown) could be used to center the drill bit 130 in the cannula 28 and ensure that the pilot hole 132 extends along the axis 162.

Figure 20:
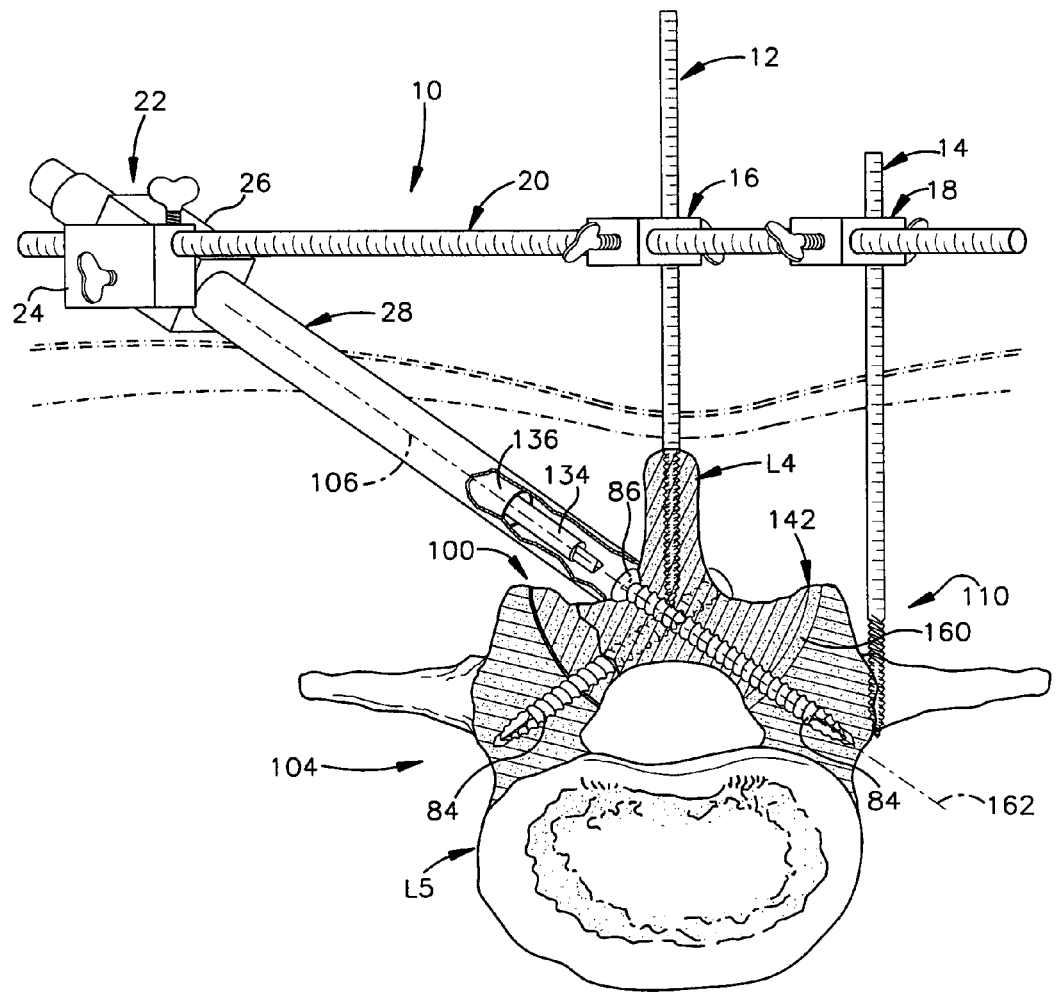

As shown in FIG. 20, the self-tapping second screw 84 is then inserted into the cannula 28 and screwed into the pilot hole 132 using the driver 134. In the illustrated embodiment, the head 86 of the screw 84 has a maximum outer diameter that matches the inner diameter of the second cannula 136 to aid in keeping the screw aligned on the axis 162 during implantation. Further, the illustrated screw head 86 has a triangular receptacle for receiving the triangular tip on the driver 134, although it should be understood that the receptacle and the corresponding driver tip could utilize a different geometry. The screw 84 is advanced until the head 86 seats against the lamina on the first side 104 of the L4 vertebrae. Fluoroscopic guidance coupled with the aforementioned calculation to select the length $L_2$ of the screw ensures that the distal tip of the screw does not penetrate beyond the cortex of the L5 vertebrae. As implanted, the second screw 84 extends across the facet joint 142 and the bone graft material 160 in the facet joint connect the inferior articular process of the L4 vertebrae to the superior articular process of the L5 vertebrae.

With the second screw 84 implanted, the cannula 28 is removed from the skin 108 and the thumbscrew 74 is released to allow relative movement of the first and second block members 24 and 26. The second block member 26 is then swiveled to aim the centerline 106 of the cannula 28 along a fourth axis 170 (FIG. 22) that extends toward the facet joint 100 on the first side 104 of the vertebrae. In order to aim the cannula 28 toward the facet joint 100, the other thumbscrews 54 may also be released to allow additional movement of the swivel block assembly 22. Releasing the other thumbscrews 54 may allow the cannula to be positioned over the existing incision while being aimed toward the facet joint 100 along the axis 170 so that the same incision can be utilized again.

Figure 21:
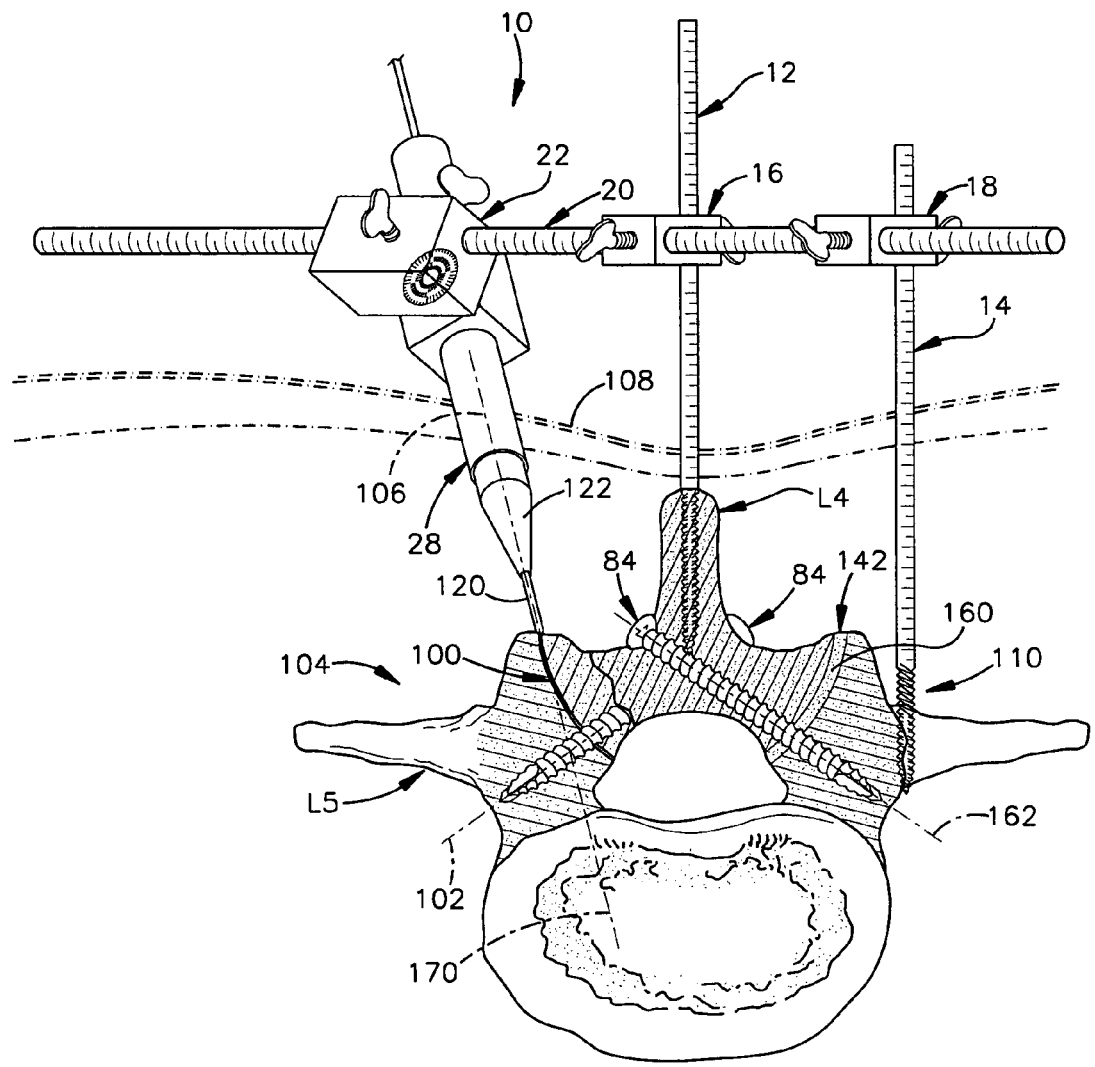
Figure 22:
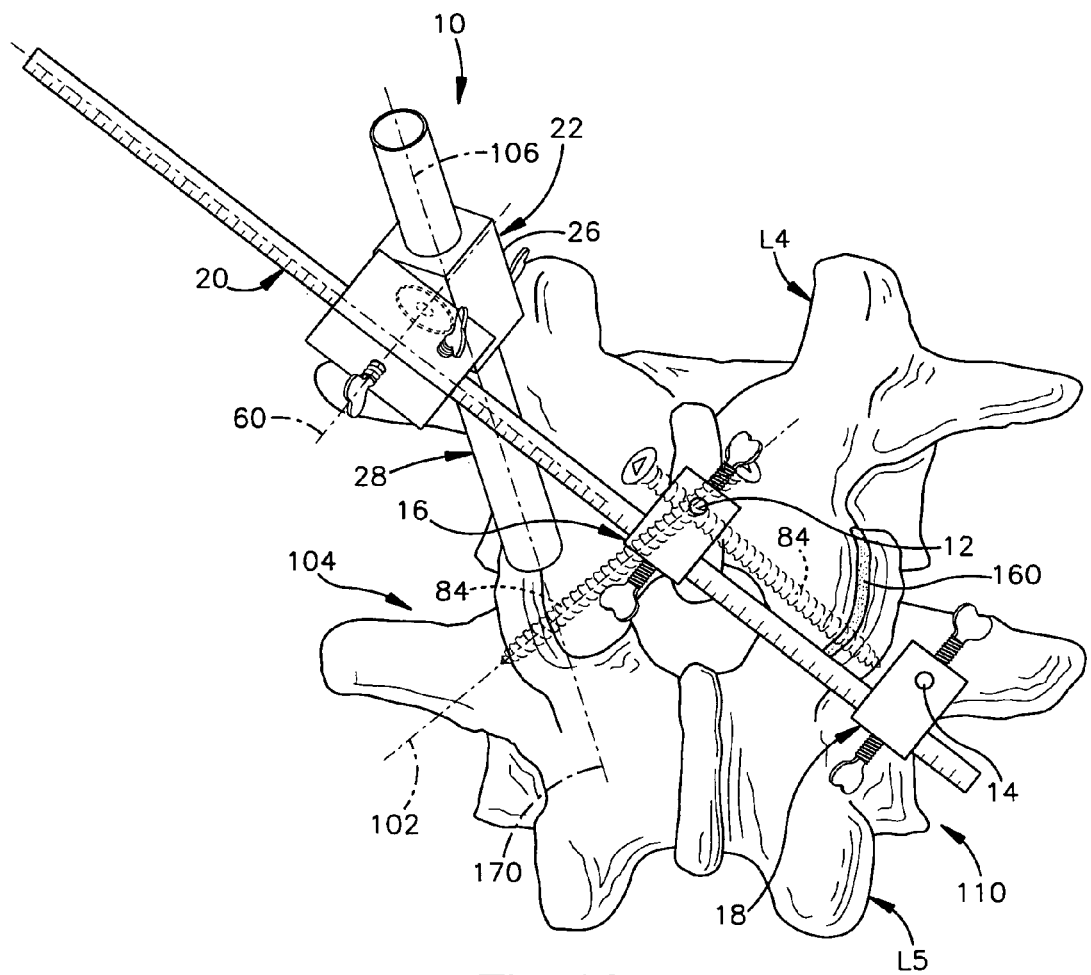
FIG. 22 is a schematic posterior view of the apparatus.
Figure 23:
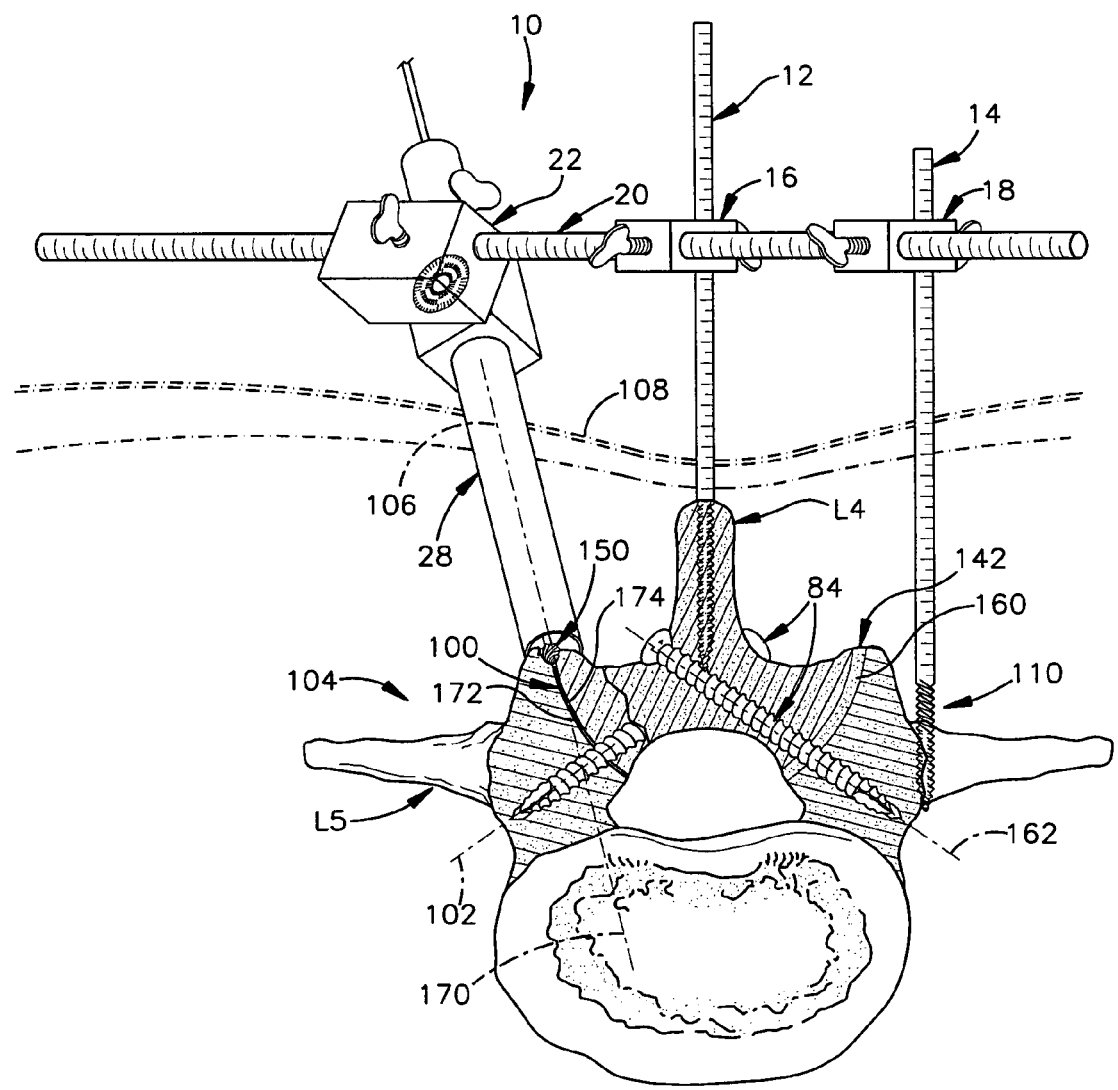
FIGS. 23 and 24 are views similar to FIG. 21 illustrating additional steps.

After tightening all of the thumbscrews 54 and 74 to secure the components of the apparatus 10 in the positions shown in FIG. 21, the guidewire 120 (or Jamshidi needle, etc.) is passed through the incision along the axis 170 to the surface of the facet joint 100 on the first side 104 of the vertebrae under fluoroscopic guidance. Next, the blunt obturator 122 is passed over the guidewire 120 to create subcutaneous space for the cannula 28 along the axis 170. The cannula 28, which is guided for movement along the axes 106 and 170 by virtue of the passage 64 through the second block member 26, is then passed over the obturator 122 and the guidewire 120. The cannula 28 is moved along the axes 106 and 170 until the distal end of the cannula docks against the surface of the facet joint 100 as shown in FIGS. 22 and 23. The guidewire 120 and the obturator 122 are then removed from the cannula 28.

After ensuring that all of the thumbscrews 54 and 74 are secure and that the alignment of the axis 170 is correct, the burring bit 150 (FIG. 23) is inserted into the cannula 28. The burring bit 150 is rotated by a drill (not shown) to burr the opposing surfaces 172 and 174 of the inferior articular process and the superior articular process on the first side 104 of the L4 and L5 vertebrae, respectively. Burring these surfaces 172 and 174 widens the facet joint 100 so that a bone graft material is more easily placed into the facet joint. It is contemplated that the cannula 28 may be moved slightly along the facet joint 100 during the burring process in order to access a larger area of the facet joint with the burring bit 150. It should be noted that care must be taken to burr around, but not contact, the first screw 84 that was previously implanted across the facet joint 100 on the first side 104 of the vertebrae.

Figure 24:
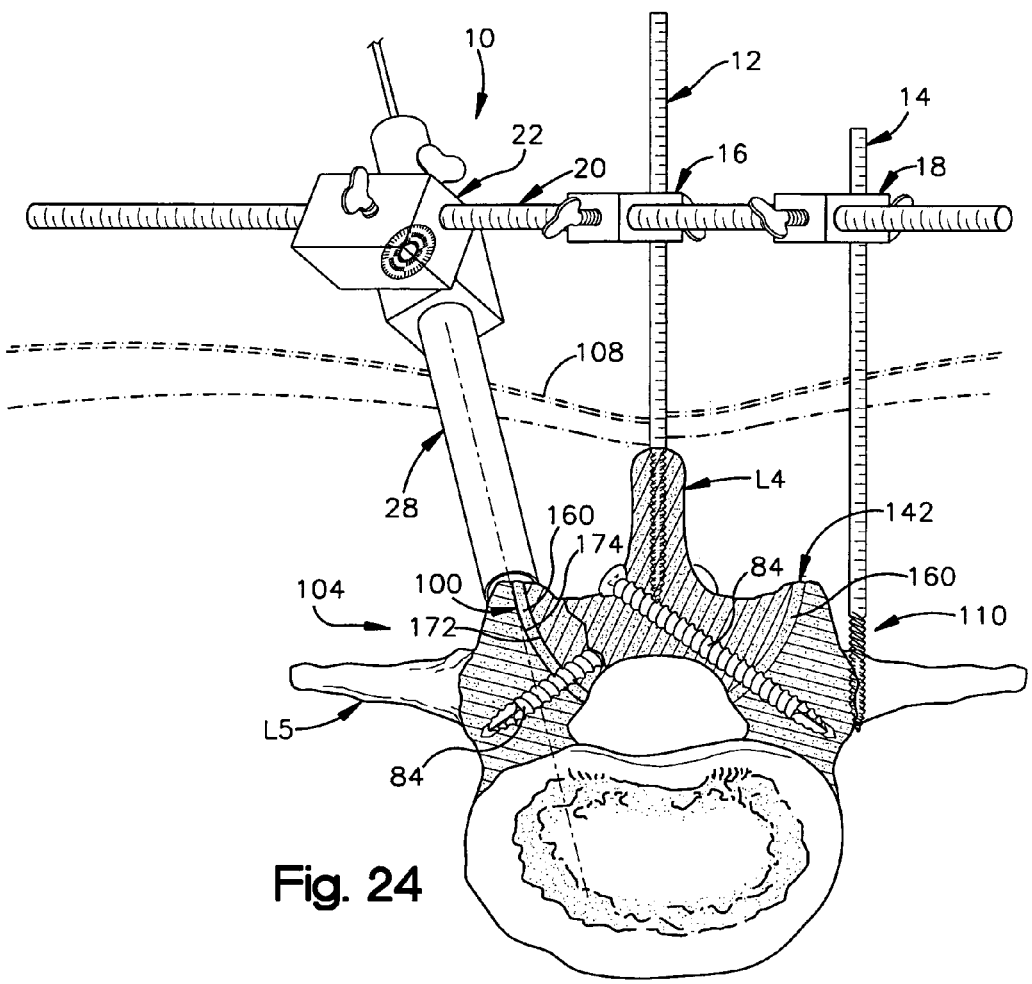
Figure 25:
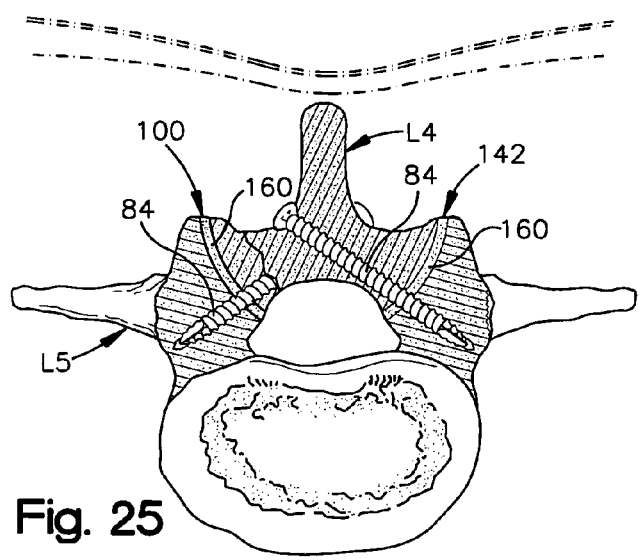
FIG. 25 is a view similar to FIG. 24 illustrating the facet screws implanted across the facet joints in the adjacent vertebrae.

After the articular surfaces 172 and 174 of the facet joint 100 on the first side 104 of the vertebrae have been burred out around the first screw 84, bone graft (or bone substitute) material 160 (FIG. 24) for helping to fuse the L4 and L5 vertebrae is placed into the facet joint 100 through the cannula 28. The bone graft material 160 may be fed into the facet joint using any known suitable instrument(s). The cannula 28 is then removed from the incision on the first side 104 of the vertebrae and the first and second K-wires 12 and 14 are removed from the L5 and L4 vertebrae, respectively. The incisions are then closed. As shown in the completed view of FIG. 24, with the two screws 84 implanted across the facet joints 100 and 142 and the bone graft material 160 placed into both of the facet joints, fusion of the L4 and L5 vertebrae will take place over the next few months.

Figure 26:
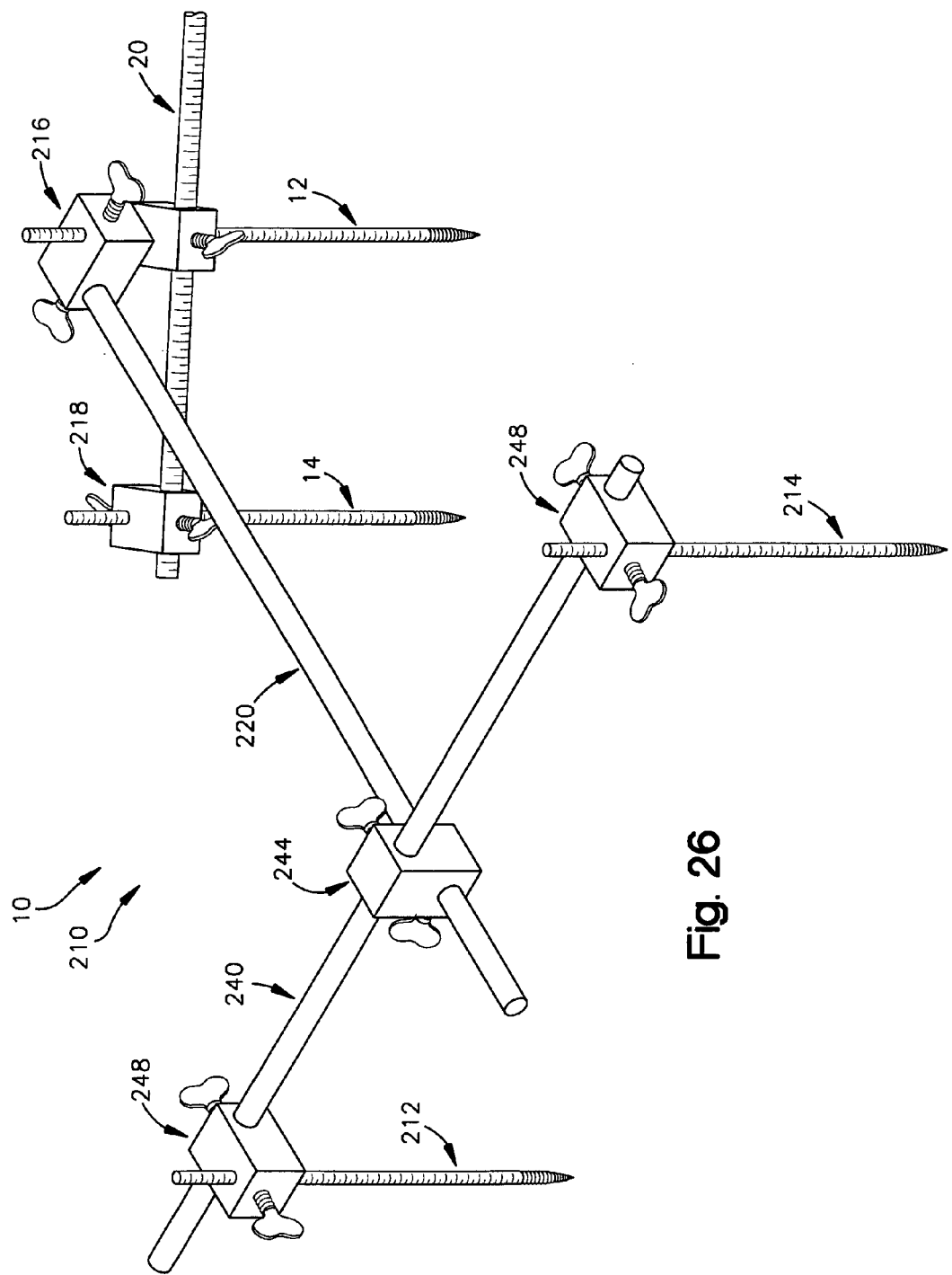
FIG. 26 is a perspective view of the apparatus of FIG. 1 further including an added support apparatus.
Figure 33:
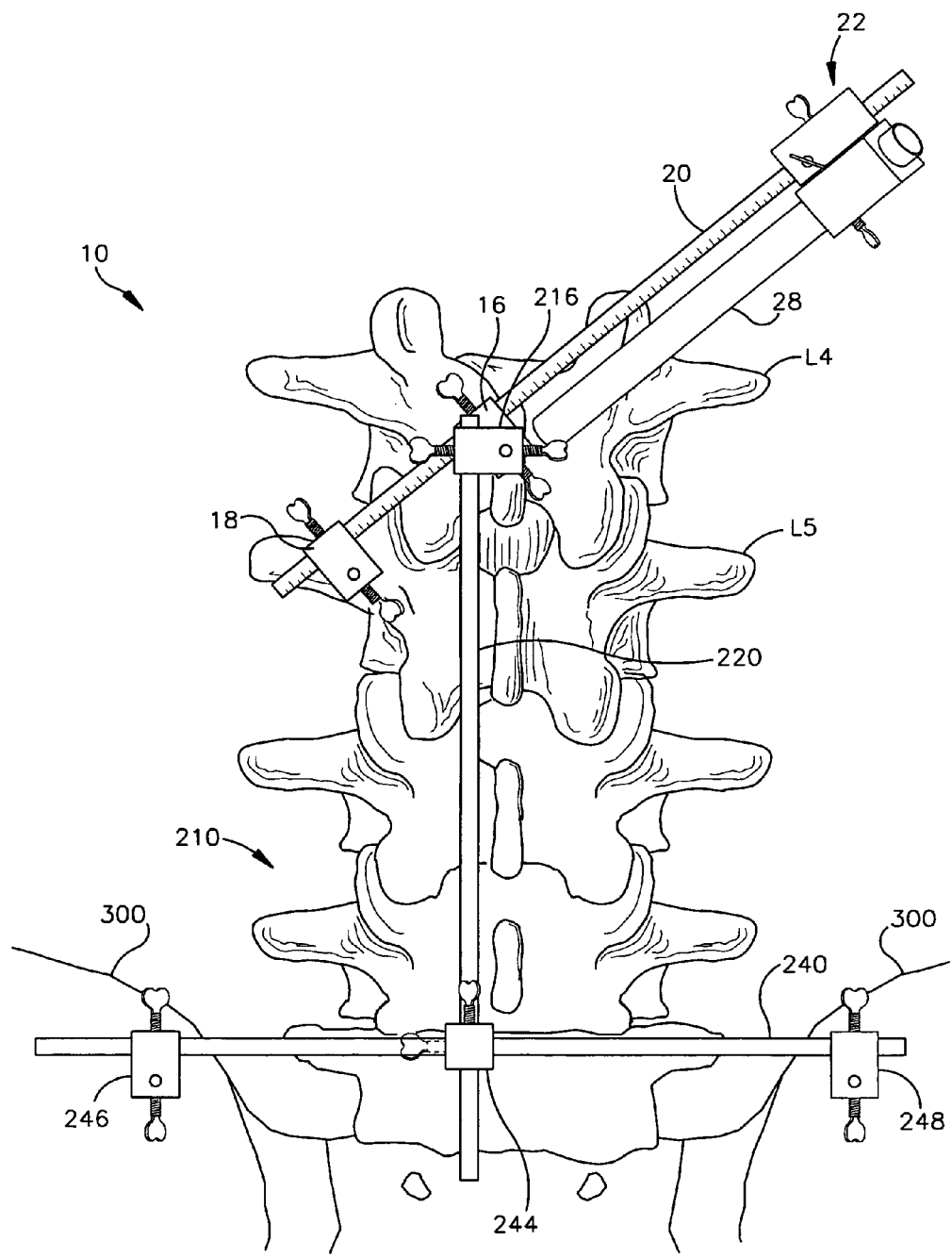
FIG. 33 is a schematic posterior view of adjacent lumbar vertebrae and components of the apparatus of FIG. 26 at an early stage of another inventive method for placing a facet screw across a facet joint.
Figure 34:
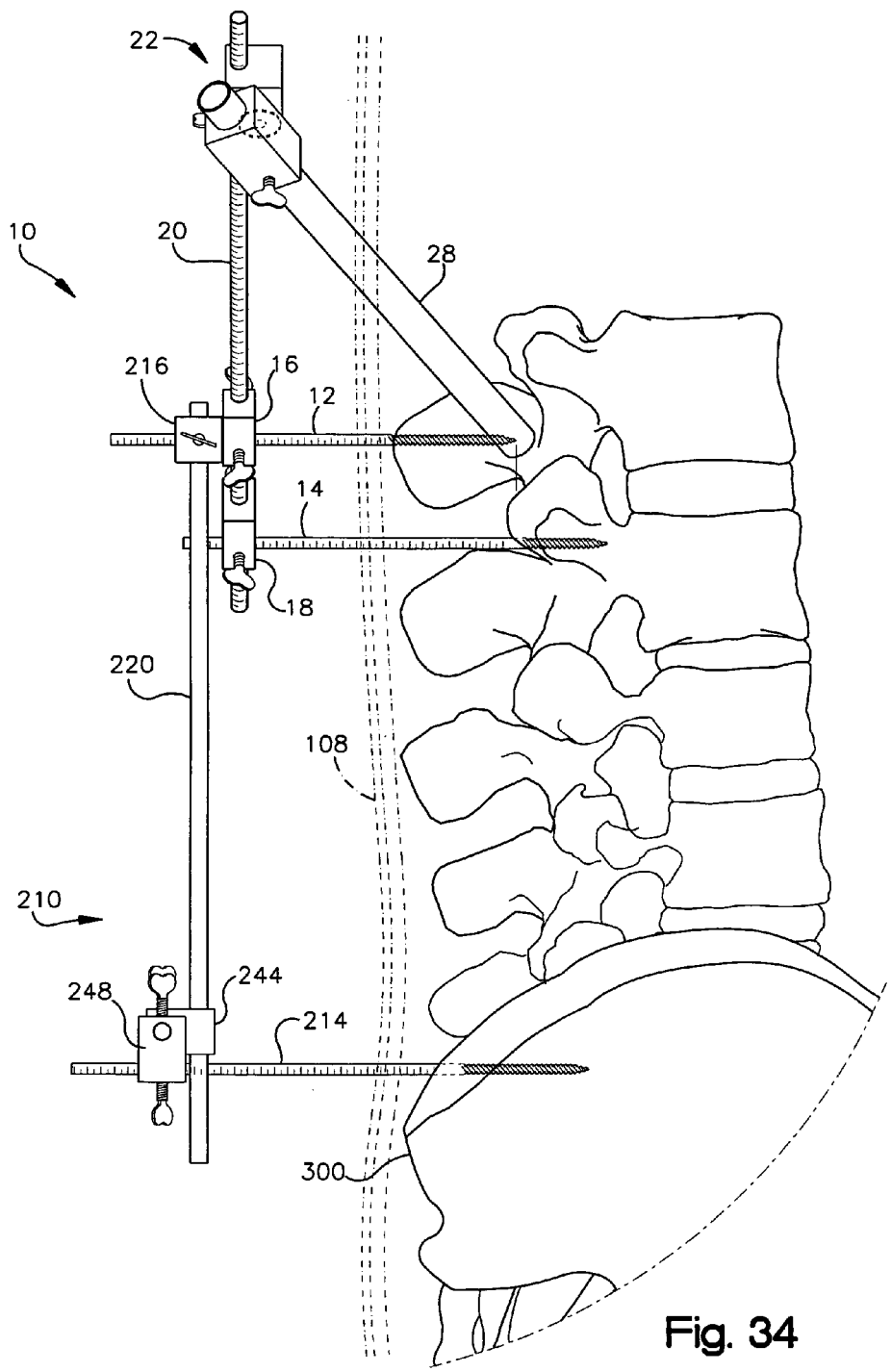
FIG. 34 is a schematic side view of FIG. 33.

As representative of another variation of the present invention, FIG. 26 illustrates a support apparatus 210 for use with the apparatus 10 of FIG. 1. The support apparatus 210 may include third and fourth Kirschner wires 212 and 214, first and second support blocks 216 and 244, third and fourth fixation blocks 246 and 248, a second rod member 220, and a third rod member 240. The third and fourth K-wires 214 and 216 may be secured to any suitable structure, such as either illiac crest 300 of the pelvic girdle of the hip or other bony landmark, as may be seen in FIGS. 33 and 34.

The support apparatus 210 thus acts as a supplementary support structure that may complement the apparatus 10 during the above set out surgical procedures. Since the first K-wire 12 is secured to the center of the spinous process of the L4 vertebrae throughout the facet screw placement and vertebral fusion procedures set out above, the apparatus 210 initially secures the apparatus 10 and may remain in place to continually secure the apparatus 10 throughout the procedure. For example, the apparatus 210 may be secured to the first K-wire 12 subsequent to the first and second fixation blocks 16 and 18 being secured to the first and second K-wires 12 and 14 and remain there throughout a surgical procedure.

Figures 27, 27A, 28, 28A:
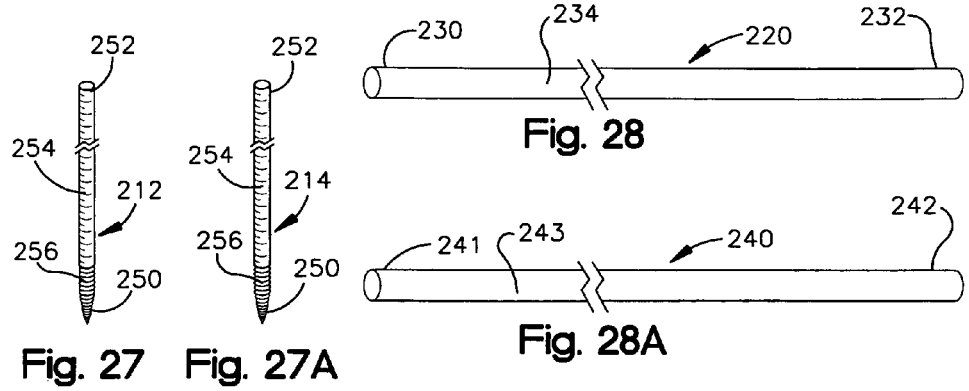
FIG. 27 is a perspective view of a component of the support apparatus of FIG. 26.
FIG. 27A is a perspective view of another component of the support apparatus of FIG. 26.
FIG. 28 is a perspective view of another component of the support apparatus of FIG. 26.
FIG. 28A is a perspective view of another component of the support apparatus of FIG. 26.

As may be seen in FIG. 28, the second rod member 220 is a cylindrical component that may be hollow or solid, square or rectangular, and made from any suitable metal or plastic. The second rod member 220 has oppositely disposed first and second ends 230 and 232 and an outer diameter of 4 to 7 mm. The second rod member 220 includes an outer surface 234.

As may be seen in FIG. 28A, the third rod member 240 is a cylindrical component that may be hollow or solid, square or rectangular, and made from any suitable metal or plastic. The third rod member 240 has oppositely disposed first and second ends 241 and 242 and an outer diameter of 4 to 7 mm. The third rod member 240 includes an outer surface 243.

The third and fourth K-wires 212 and 214 (FIGS. 27 and 27A) are identical parts, although it should be understood that the K-wires could have different sizes or shapes. Each of the third and fourth K-wires 212 and 214 is an elongate rod made of a biocompatible metal or other suitable material with an outer diameter of 2 to 4 mm. As shown in FIGS. 27 and 27A, each K-wire 212 and 214 has oppositely disposed distal and proximal ends 250 and 252 and a cylindrical outer surface 254 extending between the ends. The distal end 250 of each of the third and fourth K-wires 212 and 214 includes self-tapping threads 256. The cylindrical outer surface 254 of each of the third and fourth K-wires 212 and 214 may include graduations or other suitable means for measuring axial lengths along each K-wire for measuring the depth of each K-wire's penetration into the skin, similar to the first and second K-wires 12 and 14.

Figures 29, 30:
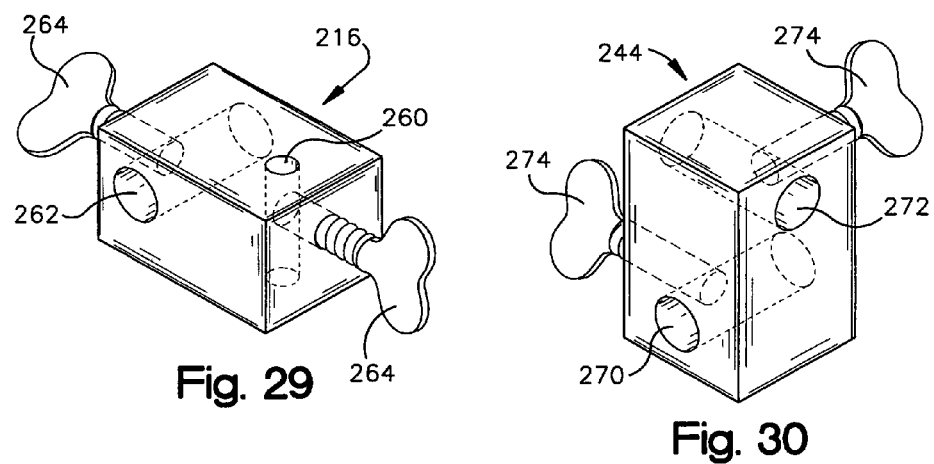
FIG. 29 is a perspective view of another component of the support apparatus of FIG. 26.
FIG. 30 is a perspective view of another component of the support apparatus of FIG. 26.

The first support block 216 (FIG. 29) is a generally rectangular part made of any suitable metal or plastic. The first support block 216 includes perpendicularly extending first and second passages 260 and 262. The first and second passages 260 and 262 are offset from each other by a predetermined amount and thus do not intersect. In the assembled condition of FIG. 26, the first K-wire 12 extends into the first passage 260 in the first support block 216 and the second rod member 220 extends into the second passage 262.

The first support block 216 further includes threaded fasteners in the form of thumbscrews 264 that extend into the first and second passages 260 and 262 for securing the first K-wire 12 and the second rod member 220 in the first and second passages 260 and 262, respectively. It should be understood, however, that other suitable means for securing the first K-wire 12 and the second rod member 220 to the first support block 216, such as clamps, latches, ratchet mechanisms, etc., could also be used, and that the securing means could be positioned on the exterior of the first support block.

The second support block 244 (FIG. 30) is a generally rectangular part made of any suitable metal or plastic. The second support block 244 includes perpendicularly extending first and second passages 270 and 272. The first and second passages 270 and 272 are offset from each other by a predetermined amount and thus do not intersect. In the assembled condition of FIG. 26, the second rod member 220 extends into the first passage 270 in the second support block 244 and the third rod member 240 extends into the second passage 272.

The second support block 244 further includes threaded fasteners in the form of thumbscrews 274 that extend into the first and second passages 270 and 272 for securing the second rod member 220 and the third rod member 240 in the first and second passages 270 and 272, respectively. It should be understood, however, that other suitable means for securing the second rod member 220 and the third rod member 240 to the second support block 244, such as clamps, latches, ratchet mechanisms, etc., could also be used, and that the securing means could be positioned on the exterior of the second support block.

Figures 31, 32:
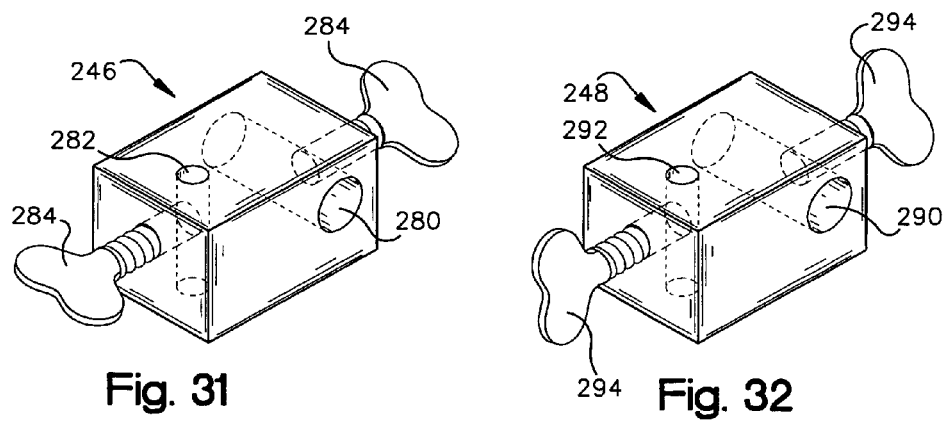
FIG. 31 is a perspective view of another component of the support apparatus of FIG. 26.
FIG. 32 is a perspective view of another component of the support apparatus of FIG. 26.

The third and fourth fixation blocks 246 and 248 (FIGS. 31 and 32) are also identical components, although it should be understood that certain aspects of the fixation blocks need not be identical. Each of the third and fourth fixation blocks 246 and 248 is a generally rectangular part made of any suitable metal or plastic. The third fixation block 246 (FIG. 31) includes perpendicularly extending first and second passages 280 and 282. The third and fourth passages 280 and 282 are offset from each other by a predetermined amount and thus do not intersect. In the assembled condition of FIG. 26, the third rod member 240 extends into the first passage 280 in the third fixation block 246 and the third K-wire 212 extends into the second passage 282.

The third fixation block 246 further includes threaded fasteners in the form of thumbscrews 284 that extend into the first and second passages 280 and 282 for securing the third rod member 244 and the third K-wire 212 and in the first and second passages 280 and 282, respectively. It should be understood, however, that other suitable means for securing the third rod member 244 and the third K-wire 212 to the third fixation block 246, such as clamps, latches, ratchet mechanisms, etc., could also be used, and that the securing means could be positioned on the exterior of the third fixation block.

In an identical fashion to the third fixation block 246, the fourth fixation block 248 includes perpendicularly extending first and second passages 290 and 292 that are offset from each other by a predetermined amount and thus do not intersect. The predetermined amount of offset between the first and second passages 290 and 292 in the fourth fixation block 248 is the same as the predetermined amount of offset between the first and second passages 280 and 282 in the third fixation block 246. In the assembled condition of FIG. 26, the third rod member 240 extends into the first passage 290 in the fourth fixation block 248 and the fourth K-wire 214 extends into the second passage 292.

The fourth fixation block 248 further includes threaded fasteners in the form of thumbscrews 294 that extend into the first and second passages 290 and 292 for securing the third rod member 240 and the fourth K-wire 214 in the first and second passages 290 and 292, respectively. It should be understood, however, that other suitable means for securing the third rod member 240 and the fourth K-wire 214 to the fourth fixation block 248, such as clamps, latches, ratchet mechanisms, etc., could also be used, and that the securing means could be positioned on the exterior of the fourth fixation block.

Figure 35:
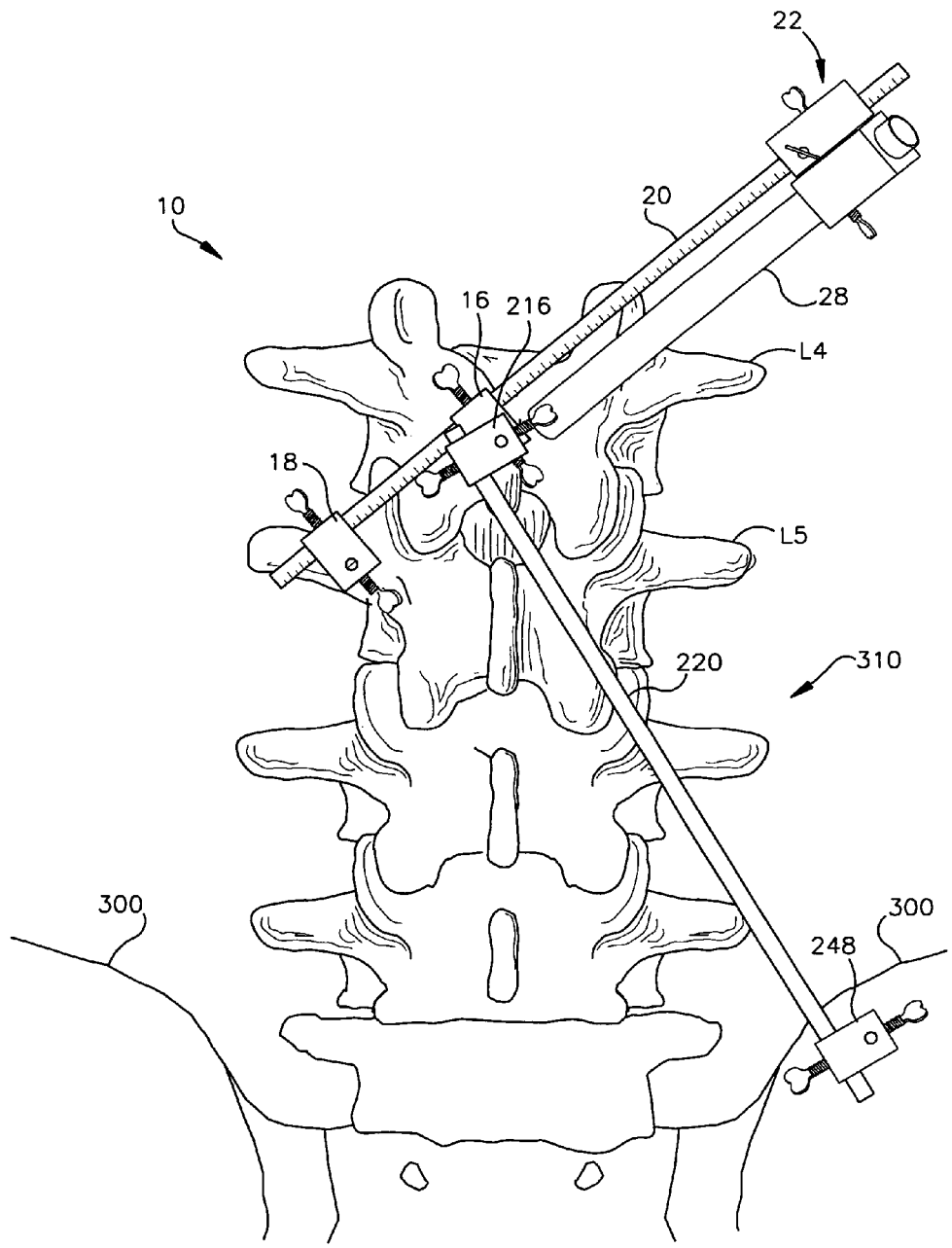
FIG. 35 is a schematic posterior view of adjacent lumbar vertebrae and components of an example variation of the apparatus of FIG. 26 at an early stage of still another inventive method for placing a facet screw across a facet joint.

As representative of still another variation of the present invention, FIG. 35 illustrates another support apparatus 310 for use with the apparatus 10 of FIG. 1. The support apparatus 310 may include the third or fourth Kirschner wire 212 or 214 of the apparatus 210, the first support block 216 of the apparatus 210, the third or fourth fixation block 246 and 248, and the second rod member 220 of the apparatus 210. The third or fourth K-wire 214 and 216 may be secured to any suitable structure, such as either side of the hip bone 300 (the second side of the hip bone 300 shown in FIG. 35).

The support apparatus 310, similar to the support apparatus 210, acts as a supplementary support structure that may complement the apparatus 10 during the above set out surgical procedures. Again, since the first K-wire 12 is secured to the center of the spinous process of the L4 vertebrae throughout the facet screw placement and vertebral fusion procedure set out above, the apparatus 310 initially secures the apparatus 10 and may remain in place to continually secure the apparatus 10 throughout the procedure. The support apparatus 310 provides a simpler alternative to the support apparatus 210, since the support apparatus 310 has fewer components than the support apparatus 210.

It should be understood to those skilled in the art that the apparatuses 10, 210, and/or 310 could be used to implant screws for a variety of procedures using a transarticular (rather than translaminar) approach directly across the facet joints. Such an application could be accomplished by simply varying the placement of the K-wires 12 and 14 to achieve the necessary screw trajectories. It is contemplated that the implantation of transarticular screws may be best accomplished by inserting the first K-wire 12 into the lamina a few millimeters lateral of the spinous process rather than into the spinous process itself. It should be noted that the swivel block assembly 22 could be positioned between the fixation blocks 16 and 18 along the rod member 20 to aid with placement of direct (or transarticular) facet screws.

The present invention described herein thus provides apparatuses and a minimally invasive methods for placing screws either directly across the facet joints of adjacent vertebrae or indirectly across the facet joints through the lamina (i.e. translaminar) as both a primary means for spinal fixation and as a secondary means for fixation to augment anterior fusion or pedicle screw fixation instrumentation. It is contemplated that the apparatuses could also be used to guide implantation for a variety of other orthopedic screws in the spine as well as other bones. Significantly, the present invention provides for the accurate and repeatable placement of facet screws and for fusing adjacent vertebrae in a minimally invasive procedure that saves time during surgery and is less traumatic to the patient.

From the above description of the invention, those skilled in the art will perceive improvements, changes and modifications. Such improvements, changes and modifications within the skill of the art are intended to be covered by the appended claims.

Having described the invention, I claim:

1. An apparatus for placing screws through a cannula and across a facet joint between adjacent first and second vertebrae, said apparatus comprising:
   a first K-wire for inserting into a spinous process of the first vertebrae;
   a first fixation block removably connected to said first K-wire;
   a second K-wire for inserting into a transverse process of the second vertebrae;
   a second fixation block removably connected to said second K-wire;
   a first rod member removably connected to both said first and second fixation blocks; and
   a support apparatus secured to a single K-wire for further securing said first and second K-wires to the first and second vertebrae, wherein said support apparatus includes a support block, a third fixation block, and a third K-wire, said support block securing said support apparatus to said first K-wire, said third fixation block securing a second end of said support apparatus to said third K-wire.

2. The apparatus of claim 1 further including a swivel assembly for angularly adjusting a distal end of the cannula to a position adjacent the facet joint.

3. The apparatus of claim 1 wherein said support apparatus further includes a second rod member for securing said support block to said third fixation block.

4. The apparatus of claim 3 wherein said support block and said third fixation block are both secured to said second rod member by thumbscrews.

5. The apparatus of claim 3, wherein said support block for securing said support apparatus to said first K-wire comprises a first support block secured to a first end of said second rod member, a second support block secured to a second end of said second rod member helping to secure said third K-wire to said support apparatus.

6. An apparatus for placing translaminar screws across a facet joint between adjacent first and second vertebrae in a minimally invasive surgical procedure, said apparatus comprising:
   a first K-wire for inserting into a spinous process of the first vertebrae;
   a second K-wire for inserting into a transverse process of the second vertebrae;
   a first fixation block having perpendicularly extending first and second passages, said first K-wire extending into said first passage in said first fixation block
   a second fixation block having perpendicularly extending first and second passages, said second K-wire extending into said first passage in said second fixation block;
   a first support block having perpendicularly extending first and second passages, said first K-wire extending consecutively through said first passage in said first fixation block and said first passage in said first support block;
   a first rod member extending through said second passage in said first fixation block and said second passage in said second fixation block;
   a second rod member for further securing said first and second fixation blocks to the first and second vertebrae, said second rod member extending through said second passage in said first support block; and
   a cannula for implanting the translaminar screws across a facet joint between the first and second vertebrae.

7. The apparatus of claim 6 further including a swivel block assembly comprising relatively movable first and second block members, said first block member having a passage for receiving said first rod member.

8. The apparatus of claim 6 further including a second support block for receiving said second rod member, said second support block adapted to further secure said first and second fixation blocks to the first and second vertebrae.

9. The apparatus of claim 8 further including a third K-wire for inserting into a portion of a pelvic bone or other bony landmark, said second support block being secured to said third K-wire.

10. The apparatus of claim 8 further including a third rod member extending through said second support block, said third rod member being secured to a third K-wire and a fourth K-wire, said third and fourth K-wires being adapted to be secured to a portion of a pelvic bone or other bony landmark.

11. The apparatus of claim 10, wherein the second rod member and the third rod member extend perpendicular to one another.

12. The apparatus of claim 6 wherein said first and second K-wires include graduations for measuring axial length along said K-wires.

13. The apparatus of claim 6 wherein said first rod member includes graduations for measuring axial length along said first rod member.

14. The apparatus of claim 6 further including a swivel block assembly comprising relatively rotatable first and second block members, said second block member having a passage for receiving said cannula.

15. The apparatus of claim 6 wherein said first fixation block includes a first thumbscrew for securing said first K-wire to said first fixation block and a second thumbscrew for securing said first rod member to said first fixation block.

16. The apparatus of claim 6 wherein said first support block includes a first thumbscrew for securing said first K-wire to said first support block and a second thumbscrew for securing said second rod member to said first support block.

17. The apparatus of claim 6, wherein the cannula extends along a plane that is parallel to the first rod member, the cannula rotating relative to the first rod member in the plane.

* * * * *